(12) United States Patent
Barrientos et al.

(10) Patent No.: US 11,179,474 B1
(45) Date of Patent: *Nov. 23, 2021

(54) NANOPARTICLE-BASED LIVER-TARGETING THERAPY AND IMAGING

(71) Applicant: MIDATECH LIMITED, Cardiff (GB)

(72) Inventors: Africa Garcia Barrientos, Sopelana (ES); Esther de Torres Dominguez, Elgoibar (ES)

(73) Assignee: MIDATECH Limited, Cardiff (GB)

( * ) Notice: Subject to any disclaimer, the term of this patent is extended or adjusted under 35 U.S.C. 154(b) by 177 days.

This patent is subject to a terminal disclaimer.

(21) Appl. No.: 15/743,970

(22) PCT Filed: Jul. 25, 2016

(86) PCT No.: PCT/EP2016/067682
§ 371 (c)(1),
(2) Date: Jan. 11, 2018

(87) PCT Pub. No.: WO2017/017063
PCT Pub. Date: Feb. 2, 2017

(30) Foreign Application Priority Data

Jul. 24, 2015 (GB) .................................. 1513103

(51) Int. Cl.
*A61K 47/69* (2017.01)
*A61K 47/64* (2017.01)
*A61K 9/51* (2006.01)

(52) U.S. Cl.
CPC ............ *A61K 47/6929* (2017.08); *A61K 9/51* (2013.01); *A61K 47/64* (2017.08)

(58) Field of Classification Search
CPC combination set(s) only.
See application file for complete search history.

(56) References Cited

U.S. PATENT DOCUMENTS

| | | | |
|---|---|---|---|
| 8,388,937 B2 | 3/2013 | Ahn et al. | |
| 9,598,479 B2* | 3/2017 | Rademacher | ............ A61P 35/00 |
| 10,300,022 B2* | 5/2019 | Rademacher | ...... A61K 39/3955 |
| 2008/0267979 A1 | 10/2008 | Lazar et al. | |
| 2010/0034735 A1 | 2/2010 | Chen et al. | |
| 2010/0203612 A1 | 8/2010 | Cheol et al. | |
| 2012/0270238 A1 | 10/2012 | Moro et al. | |

FOREIGN PATENT DOCUMENTS

| | | |
|---|---|---|
| CN | 103784979 | 5/2014 |
| EP | 2305310 | 4/2011 |
| WO | WO200232404 | 4/2002 |
| WO | WO2004108165 | 12/2004 |
| WO | WO2005091704 | 10/2005 |
| WO | WO2005116226 | 12/2005 |
| WO | WO2006037979 | 4/2006 |
| WO | WO2007015105 | 2/2007 |
| WO | WO2007122388 | 11/2007 |
| WO | 2011154711 | 12/2011 |
| WO | 2011156711 | 12/2011 |
| WO | WO2013176468 | 11/2013 |
| WO | 2014125256 | 8/2014 |
| WO | 2016075211 | 5/2016 |
| WO | 2017144551 | 8/2017 |

OTHER PUBLICATIONS

Yan et al (Tumor Biology, 2015, 36:55-67; published online Nov. 26, 2014).*
Adokoh et al (Biomacromolecules, 2014, 15:3802-3810).*
Garg et al (AAPS PharmSciTech, 2013, 14:1219-1226).*
Yan et al (Tumor Biology, Jan. 2015, 36:55-67).*
Bergen et al (Macromolecular Bioscience, 2006, 6:506-516).*
Adokoh et al. (2014) "Synthesis and Evaluation of Glycopolymeric Decorated Gold Nanoparticles Functionalized with Gold-Triphenyl Phosphine as Anti-Cancer Agents" Biomacromolecules, vol. 15, pp. 3802-3810.
Barrientos et al. (2003) "Gold Glyconanoparticles: Synthetic Polyvalent Ligands Mimicking Glycocalyx-Like Surfaces as Tools for Glycobiological Studies" Chemistry: A European Journal, vol. 9, No. 9, pp. 1909-1921.
De et al. (2014) "Synthesis of a smart Nanovehicle for Targeting Liver" *Methods in Molecular Biology*, vol. 1141, 2014, pp. 211-232.
De La Fuente et al. (2006). "Glyconanoparticles: Types, synthesis and applications in glycoscience, biomedicine and material science" *Biochemica et Biophysica Acta*, vol. 1760, pp. 636-651.
Garg et al. (2013) "Synthesis of a Smart Gold Nano-vehicle for Liver Specific Drug Delivery" *AAPS PharmSciTech*, vol. 14, No. 9, pp. 1219-1226.
Hadokoh et al. (2014) "Glypican-3 Targeted Human Heavy Chain Antibody as a Drug Carrier for Hepatocellular Carcinoma Therapy" *Biomacromolecules*, vol. 15, 3802-3810.
Hanaoka et al. (2015) "Glypican-3 Targeted Human Heavy Chain Antibody as a Drug Carrier for Hepatocellular Carcinoma Therapy"*Molecular Pharmaceutics*, vol. 12, No. 6, pp. 2151-2157.
Huang et al. (2012) "Size-Dependent Localization and Penetration of Ultrasmall Gold Nanoparticles in Cancer Cells, Multicellular Spheroids, and Tumors in Vivo" ACS *Nano*,vol. 6, pp. 4483-4493.

(Continued)

*Primary Examiner* — Laura B Goddard

(74) *Attorney, Agent, or Firm* — Carol L. Francis; Rudy J. Ng; Bozicevic, Field & Francis LLP

(57) ABSTRACT

The invention provides a nanoparticle comprising: a core comprising a metal and/or a semiconductor; and a plurality of ligands covalently linked to the core, wherein said ligands comprise: at least one liver-targeting ligand; at least one payload ligand comprising a bioactive agent; and at least one dilution ligand comprising a carbohydrate. Also provided are pharmaceutical compositions comprising the nanoparticles, medical uses thereof, including in the treatment and imaging of liver cancers, and processes for the production of the nanoparticles.

16 Claims, 12 Drawing Sheets

Specification includes a Sequence Listing.

(56) References Cited

OTHER PUBLICATIONS

Kumara et al. (2014) "Faradaurate-940: Synthesis, Mass Spectrometry, Electron Microscopy, High-Energy X-ray Diffraction, and X-ray Scattering Study of Au~940 (20(SR)~160 (4 Nanocrystals" *ACS Nano*, 2014, vol. 8, pp. 6431-6439.

Lee et al. (2011) "Targeting of hepatocellular carcinoma with glyplcan-3-targetlng peptide llgand",*Journal of Peptide Science*, vol. 17, No. 11, pp. 763-769.

Li et al. (2015) "Preparation of magnetic resonance probes using one-pot method for detection of hepatoceilular carcinoma" *World Journal of Gastroenterology*, vol . 21, No. 14, p. 4275-4283.

Liang et al. (2014) "Smart gold nanoshells for combined cancer chemotherapy and hyperthermia" *Biomedical Materials*, vol. 9, 2014, pp. 1-11.

Mamidyala et al. (2012) "Glycomimetic Ligands for the Human Asialoglycoprotein Receptor"*J. Am. Chem. Soc.*, 2012, vol. 134(4), pp. 1978-1981.

Penadés et al. (2004) "Gold Glyconanoparticles as New Tools in Antiadhesive Therapy" *Chem. Bio. Chem.*, vol. 5, pp. 291-297.

Penadés et al. (2009) "Modulating glycosidase degradation and lectin recognition of gold Glyconanoparticles" Carbohydrate *Research*, vol. 334, pp. 1474-1478.

Shi et al. (2009) "Expression of Asialoglycoprotein Receptor 1 in Human Hepatocellular Carcinoma", *J. Histochem. Cytochem.*, 2013, vol. 61, pp. 901-909.

Zeng et al. (2015) "Construction of a cancer-targeted nanosystem as a payload of iron complexes to reverse cancer multidrug resistancet" *J. Mater. Chem. B J. Mater. Chem. B*, pp. 4345-4354.

\* cited by examiner

NANOPARTICLE-BASED LIVER-TARGETING THERAPY AND IMAGING

FIELD OF THE INVENTION

The present invention relates to nanoparticles as vehicles for the targeted delivery of agents to specific tissue types or locations, particularly for use in medicine, and includes methods for treatment of liver disorders such as liver cancer. Pharmaceutical compositions, processes for production of the nanoparticles and methods for their use are also disclosed.

BACKGROUND TO THE INVENTION

The present invention is directed at compositions and products, and methods of making and administering such compositions and products, including for the treatment of mammals and particularly humans.

Drug delivery poses several significant challenges, particularly with regard to the site of action. In the case of treatment of certain tumours, for example, there remains a need for delivery systems that are able to target anti-cancer drugs to the tumour site, while minimizing off-target effects.

Primary liver cancer is the sixth most frequent cancer globally and the second leading cause of cancer death. The most frequent liver cancer, accounting for approximately 75% of all primary liver cancers, is hepatocellular carcinoma (HCC). HCC is formed by hepatocytes that become malignant. Hepatitis B, Hepatitis C, aflatoxin B1 and the abuse of alcohol are the four agents responsible for approximately 80% of the human HCCs. Hence, underlying diseases like steatohepatitis, fibrosis and cirrhosis often complicate conventional HCC therapy. Currently, surgical resection is the major treatment option for HCC if the tumour is resectable. However, only 10-20% of HCC can be removed completely using surgery. Therefore, targeted drug delivery is of crucial interest due to both improvement of efficacy of approved chemotherapeutics and reducing their side effects (Shi B. et al., *J. Histochem. Cytochem.*, 2013, Vol. 61, pp. 901-909).

WO0232404 describes carbohydrate-coupled (including lactose-coupled) gold nanoparticles. WO2014/125256 describes nanoparticle delivery systems for use in targeting biologically active agents to the central nervous system (CNS), e.g., for treatment of CNS disorders.

Garg et al., *AAPS PharmSciTech*, 2013, Vol. 14, No. 3, pp. 1219-1226, describes a lactose surface-modified gold nanovehicle for the intracellular delivery of a fluorescent coumarin derivative to hepatic cells.

Penadés et al., *Chem. Eur. J.*, Vol. 9, pp. 1909-1921 describes the synthesis of fluorescent glyconanoparticles.

Penadés et al., *Carbohydrate Research*, Vol. 344, pp. 1474-1478 describes studies evaluating the influence of ligand density and presentation on the recognition of protein receptors using lactose-functionalised gold nanoparticles.

Penades et al., *Chem. Bio. Chem.*, Vol. 5, pp. 291-297 describes studies investigating the use of glyconanoparticles presenting lactose to reduce the progress of experimental metastasis.

There remains an unmet need for further nanoparticle delivery systems and for methods of delivering bioactive and/or detectable agents to a specific tissue or location in a subject, including for the targeted treatment of primary liver cancer. The present invention addresses these and other needs.

BRIEF DESCRIPTION OF THE INVENTION

Broadly, the present invention relates to nanoparticles provided with a liver-targeting moiety and a payload, which nanoparticles are useful as vehicles for the delivery of the payload to the liver, including to diseased cells of the liver. The payload may comprise one or more bioactive agents and/or detectable agents for therapeutic and/or imaging applications, respectively. The present inventors have surprisingly found that nanoparticles in which lactose ligands are covalently linked to the gold core via relatively long linkers of the form lactose —$(OCH_2CH_2)_m$—$(CH_2)_n$—SH exhibit in vivo and in vitro targeting to liver hepatocytes. Evidence presented in the Examples herein suggests that the lactose long-linker gold nanoparticles (GNPs) interact with the asialoglycoprotein receptor (ASGPR) expressed on hepatocytes. Without wishing to be bound by any particular theory, the present inventors believe that the combination of a relatively rigid (alkyl) linker portion proximal to the core and a relatively flexible (ethylene glycol) linker portion proximal to the lactose group provides advantageous ligand arrangement for interaction with the ASGPR and ultimately for delivery of drug payload to the liver. Moreover, the present inventors have found that certain glypican-3 binding peptides, when covalently linked to the nanoparticle core, act to target the nanoparticle to hepatocellular carcinoma cells, e.g. 7-fold targeting relative to base nanoparticles, and can provide liver targeting function to nanoparticles having, e.g., a maytansinoid DM4 chemotherapeutic payload.

Accordingly, in a first aspect the present invention relates to a nanoparticle comprising:
  a core comprising a metal and/or a semiconductor; and
  a plurality of ligands covalently linked to the core, wherein said ligands comprise:
    (i) at least one liver-targeting ligand;
    (ii) at least one payload ligand comprising a bioactive agent and/or detectable agent; and
    (iii) at least one dilution ligand comprising a carbohydrate.

Accordingly, in a related first aspect the present invention may provide a nanoparticle comprising:
  a core comprising a metal and/or a semiconductor; and
  a plurality of ligands covalently linked to the core, wherein said ligands comprise:
    (iv) at least one liver-targeting ligand;
    (v) at least one payload ligand comprising a bioactive agent; and
    (vi) at least one dilution ligand comprising a carbohydrate.

In some cases the liver-targeting ligand may be selected from: lactose, FGF-4 (fibroblast growth factor 4), c-Met (hepatocyte growth factor receptor), a glypican-3 binding agent (e.g. a glypican-3 binding peptide as disclosed in U.S. Pat. No. 8,388,937, in particular SEQ ID NO: 1 or 10 as disclosed therein, or an anti-glypican-3 antibody), an alpha-fetoprotein (AFP) receptor binding agent (e.g. an AFP receptor binding peptide as disclosed in US2012/0270238 or an anti-AFP receptor antibody), and an ASGPR binding agent (e.g. galactose, N-acetylgalactosamine, lactose, glucose, mannose, or a glycomimetic ligand such as disclosed in Mamidyala et al., *J. Am. Chem. Soc.*, 2012, Vol. 1334, No. 4, pp. 1978-1981). The liver-targeting ligand may also be an antibody or binding fragment thereof, e.g. a Fab fragment (fragment antigen-binding), single domain antibody/nanobody directed at a liver or hepatocyte target such as glypican-3, ASGPR, FGF-4, c-Met, AFP or other liver-expressed protein or liver-expressed receptor.

In some cases, the liver-targeting ligand may comprise the glypican-3 binding peptide that comprises or consists of the peptide of the amino acid sequence set forth as SEQ ID NO: 1 or 2, or is a variant thereof differing from said amino acid sequence by deletion, addition, modification or substitution of not more than 3 amino acids, wherein said variant retains at least 50% of the binding affinity to human glypican-3 of the peptide of SEQ ID NO 1 or 2. Binding affinity may be determined, for example, in a competitive binding assay in which the variant peptide competes with the peptide of SEQ ID NO: 1 or 2 for binding to human glypican-3 polypeptide.

In certain cases, the glypican-3 peptide has N-terminal acetylation and/or C-terminal amidation.

In some cases, the liver-targeting ligand (e.g. lactose or glypican-3 binding peptide) may be covalently linked to the nanoparticle core (e.g. gold core) via a linker.

In some cases, the liver-targeting ligand may be covalently linked to the core via a first linker, said first linker having a chain length of 2 to 50 atoms. In particular, the first linker may comprise a group —$(CH_2)_n$— and/or —$(OCH_2CH_2)_m$—, wherein n and m are independently ≥1. In certain cases, said first linker comprises —$(OCH_2CH_2)_m$—, wherein m is between 1 and 10, for example wherein m is in the range 5 to 9, e.g. m is 8. In certain cases, the first linker comprises —$(OCH_2CH_2)_m$—$(CH_2)_n$—, wherein m=1 to 10 and n=1 to 15. In particular, m may be in the range 3 to 7 and/or n may be in the range 5 to 12.

In some cases, the at least one liver-targeting ligand and said first linker may be selected from the group consisting of: HS—$(OCH_2CH_2)_8$—CONH-RLNVGGTYFLTTRQ (SEQ ID NO: 1); HS—$(OCH_2CH_2)_8$—CONH-RLNVGGTYFLTTRQ-$NH_2$ (SEQ ID NO: 1); HS—$(OCH_2CH_2)_8$—CONH-YFLTTRQ (SEQ ID NO: 2); HS—$(OCH_2CH_2)_8$—CONH-YFLTTRQ-$NH_2$ (SEQ ID NO: 2); HS—$(OCH_2CH_2)_6$—NH(Ac)-RLNVGGTYFLTTRQ (SEQ ID NO: 1); and HS—$(OCH_2CH_2)_6$—NH(Ac)-YFLTTRQ (SEQ ID NO: 2).

In some cases, the first linker may be bound to the core via a terminal sulphur atom (e.g. gold sulphur or gold-thiol bond).

In certain cases the liver-targeting ligand covalently linked to the core via said first linker has the structure of formula (I):

wherein said first linker is bound to the core via the terminal thiol group.

In some cases the payload ligand comprises a therapeutic agent such as a chemotherapeutic or cytotoxic compound. In certain cases the payload ligand may comprise a compound selected from the group consisting of: maytansinoid DM4, doxorubicin, irinotecan, Platinum (II), Platinum (IV), temozolomide, carmustine, camptothecin, doxorubicin, docetaxel, sorafenib, maytansine, maytansinoid DM1, monomethyl auristatin E (MMAE) and panobinostat. The payload ligand may, in some cases, be covalently linked to the core of the nanoparticle via a second linker, which may be the same or different from the first linker. In some cases, e.g. when the payload ligand comprises a thiol group, the payload ligand may be directly attached to the nanoparticle core, for example via a gold-thiol bond using the payload ligand's thiol group as the attachment site.

In some embodiments, the second linker has a chain length of 2 to 50 atoms. In particular, the second linker may comprise a group —$(CH_2)_n$— and/or —$(OCH_2CH_2)_m$—, wherein n and m are independently ≥1. In certain cases, the second linker comprises —$(OCH_2CH_2)_m$—, wherein m=1 to 10, optionally wherein m=1, 2, 3, 4, 5, or 6. In some cases, a shorter linker is preferred and m is 1. In some cases, a longer linker is preferred and m is 5.

In some cases, the second linker may be bound to the core via a terminal sulphur atom (e.g. gold sulphur or gold-thiol bond). Accordingly, in some cases the second linker comprises —$(OCH_2CH_2)_m$SH (where the linker is bound to the core via the terminal thiol group). In some cases, the second linker comprises a ω-amino group to facilitate attachment of the payload, for example via an attachment linker.

Accordingly, in some cases, the second linker comprises .NHCH$_2$CH$_2$—$(OCH_2CH_2)_m$SH, (where the linker is bound to the core via the terminal thiol group and (i.e. dotted line as in structure below) indicates the point of attachment to the bioactive or an intermediate linker). A particularly preferred second linker is:

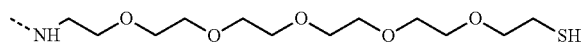

A bioactive molecule or detectable label may be bound directly to the second linker, or via an intermediate linker. Suitable intermediate linkers may be derived from dicarboxylic acids. For example, suitable intermediate linkers include succinates and malonates. For example, payload ligand and may be a ligand and of formula:

(I)

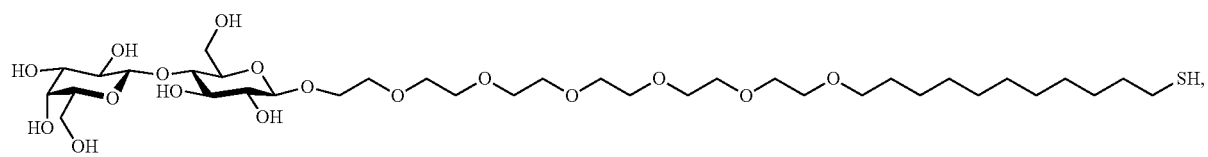

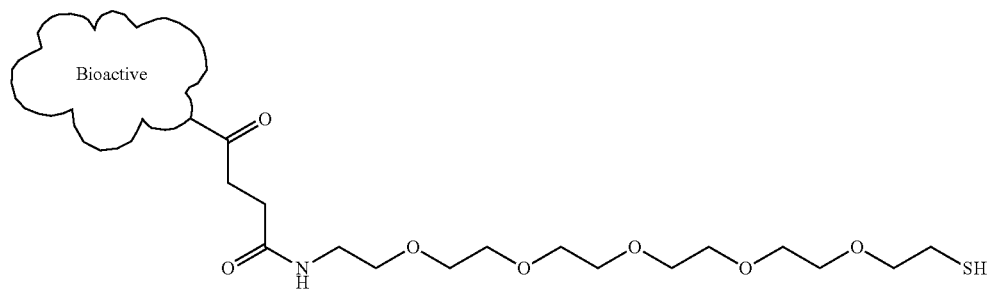 [SMILES: CC(=O)CCC(=O)NCCOCCOCCOCCOCCOCCS]

For example, in some embodiments, the nanoparticle comprises a payload ligand of formula:

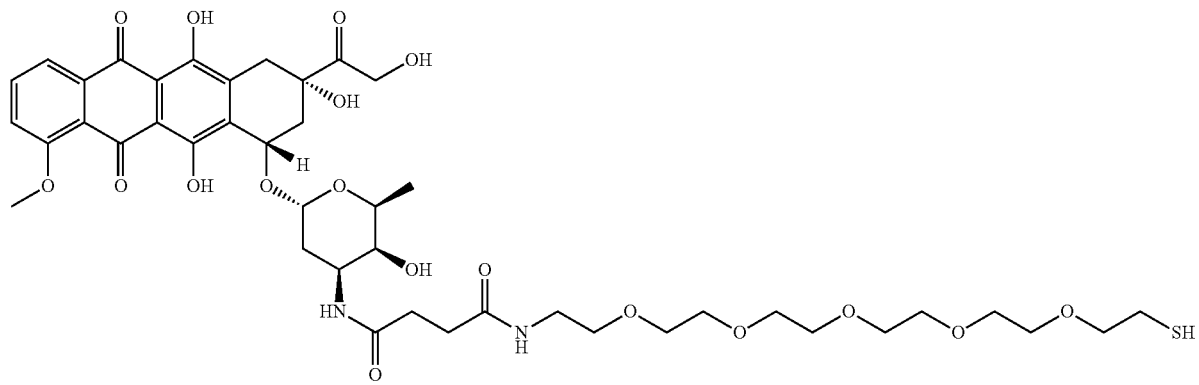 [SMILES: COc1cccc2c1C(=O)c1c(O)c3c(c(O)c1C2=O)C[C@@](O)(C(=O)CO)C[C@@H]3O[C@H]1C[C@H](NC(=O)CCC(=O)NCCOCCOCCOCCOCCOCCS)[C@H](O)[C@H](C)O1]

Some therapeutic agents may be bound by complexation, for example to a metal centre. Succinate intermediate linkers having a terminal oxygen unit may be used.

For example, in some embodiments, the nanoparticle comprises a payload ligand of formula:

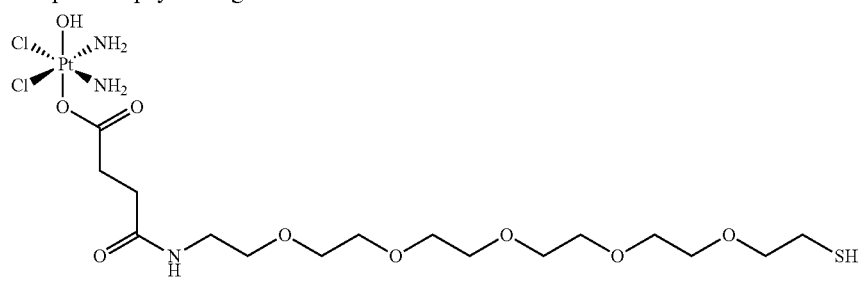

Coordination may be bidentate. For example, Pt(II) centres may be coordinated to intermediate linkers having a dicarboxylic acid moiety. For example, the intermediate linker may comprise a 2-malonate moiety.

For example, in some embodiments, the nanoparticle comprises a payload ligand of formula:

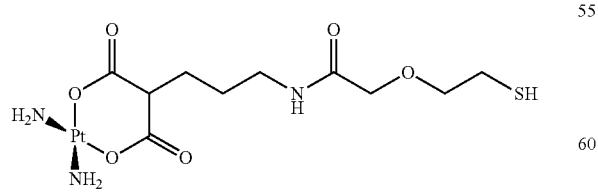

This may be synthesised by nanoparticle assembly using the malonate bearing linker, followed by subsequent complexation of the Pt(II) species.

In certain cases, the payload ligand may be selected from the group consisting of:

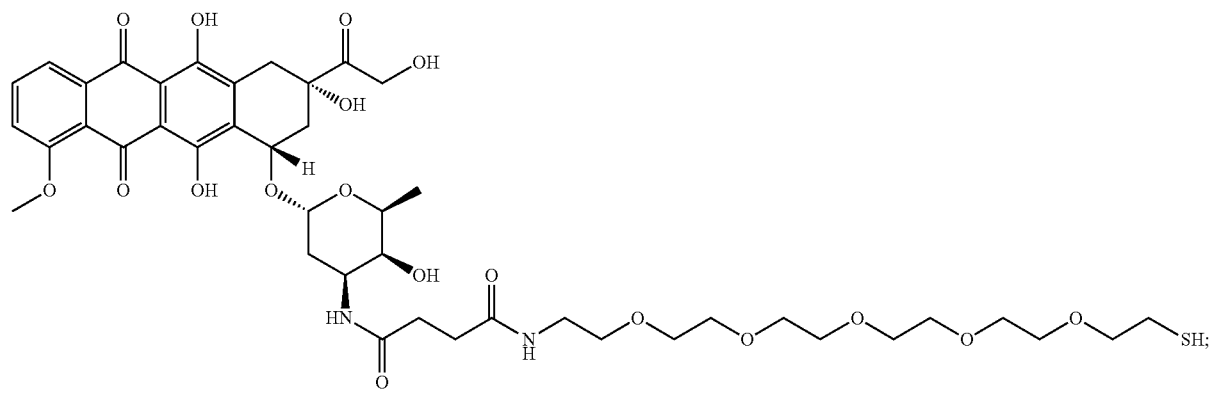
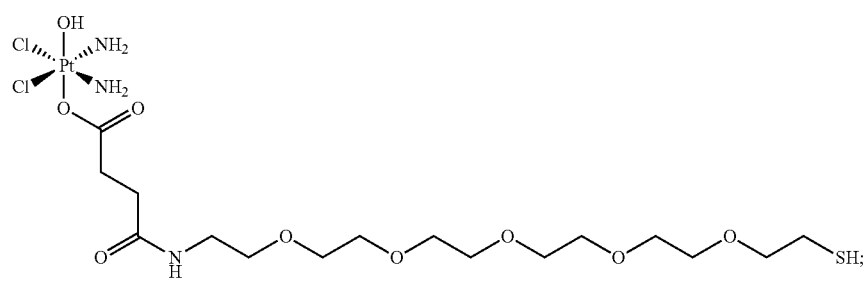
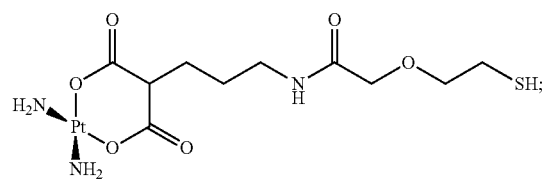
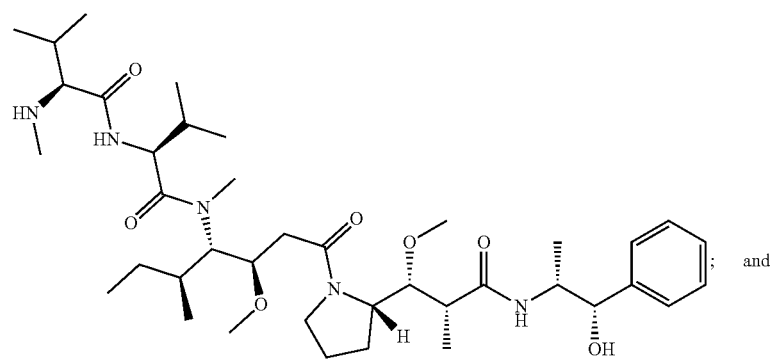
; and
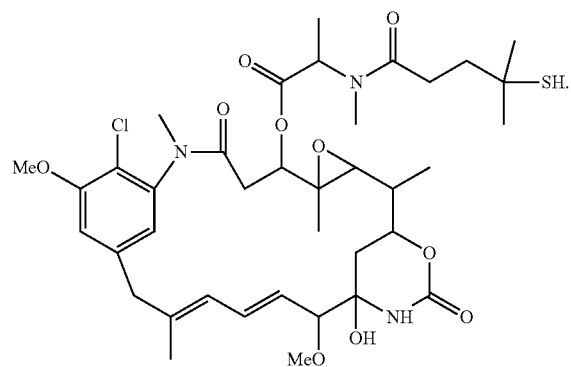 [SMILES: COc1cc2cc(c1Cl)N(C)C(=O)CC(OC(=O)C(C)N(C)C(=O)CCC(C)(C)S)C1(C)OC1C(C)C1CC(O)(NC(=O)O1)C(OC)/C=C/C=C(\C)C2]

In some embodiments, the nanoparticle comprises a payload ligand of formula:

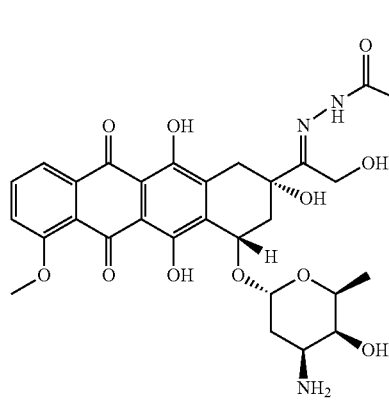
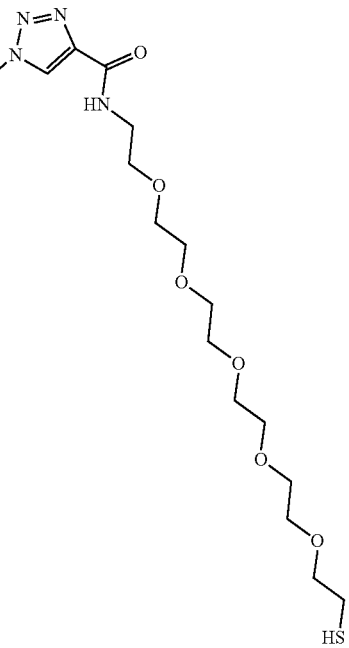

This may be synthesised by assembling a nanoparticle having a linker having a ω-pro-2-enyamide group, then effecting a 1,3-diploar cycloaddition with a bioactive derivative having a terminal azide moiety. An overview illustrating an example of the general "click chemistry" reaction scheme is shown in FIG. 1A.

In some cases the nanoparticle further comprises detectable agent or detectable label. The nanoparticle may comprise a further payload ligand, said further payload ligand comprising a detectable agent or detectable label. In particular, the detectable label may be a fluorescent label or an opto-acoustic dye.

For example, the detectable agent may be a dye, for example a near infrared dye such as a rhodamine dye (e.g. rhodamine B, sulforhodamine B) or Cy5.5. For example, the dye may be an opto-acoustic dye such as Cy7, Cy7.5, Cy8, or Li-cor® IRDye800®.

The further payload ligand may comprise a linker as described above (first and second linkers). For example, the further payload ligand may comprise a linker of formula —$(OCH_2CH_2)_m$—$(CH_2)_n$—, wherein m=1 to 10 and n=1 to 15. In particular, m may be in the range 3 to 7 and/or n may be in the range 5 to 12.

In some cases, the nanoparticle comprises a payload ligand comprising a detectable agent of formula:

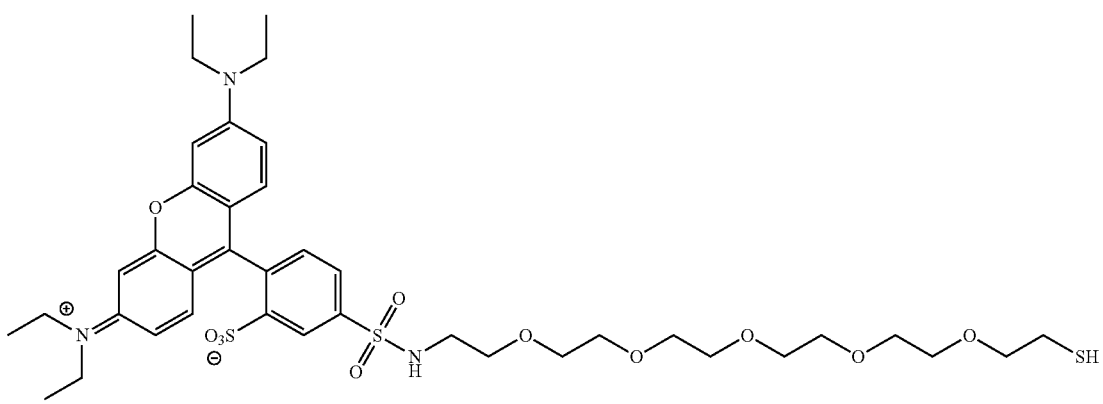

In some cases the at least one dilution ligand comprises a monosaccharide. In some cases, the dilution ligand comprises a carbohydrate having at least one six-membered ring. In particular, the monosaccharide may be glucose or galactose.

In certain cases, the at least one dilution ligand may be covalently bound to the core via a third linker. For example, the third linker may comprise a chain length of 2 to 10 atoms. The third linker may be the same or different from the first or the second linker. In some cases the third linker comprises —(CH$_2$)$_n$—, wherein n is in the range 1 to 10, e.g., 2, 3, 4, 5, 6, 7, 8, 9 or 10.

In some cases the third linker is bound to the core via a terminal sulphur atom.

In some cases the at least one dilution ligand covalently linked to the core via said third linker has the structure of formula 1, 2, 3, 4 or 5:

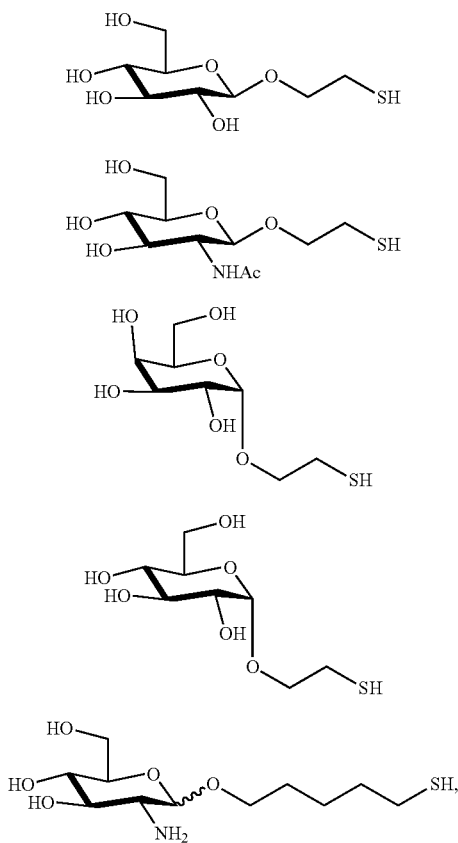

wherein said third linker is bound to the core via the terminal thiol group.

In some cases in accordance with this and other aspects of the present invention, said plurality of ligands comprise:
(i) a lactose-containing ligand or a glypican-3 binding peptide;
(ii) a doxorubicin-containing ligand or a maytansinoid DM4 ligand; and
(iii) a monosaccharide ligand comprising galactose or glucose.

In some cases in accordance with this and other aspects of the present invention, said ligands are present on the nanoparticle in the following proportions by number:
(i) said liver-targeting ligand: 1-99%
(ii) said payload ligand: 1-99%
(iii) said dilution ligand: 1-99%
(iv) said first linker: 0-99%
(v) said second linker: 0-99%.

In some cases the first linker (for attachment of the liver-targeting ligand) may be present without a liver targeting moiety. For example, in circumstances where the liver targeting moiety is attached by reacting with a first linker present on the nanoparticle (which may be preferable for example where the liver targeting moiety comprises an antibody fragment), the reaction may not completely saturate the available first linkers leaving some first linker "unreacted" on the nanoparticle.

Additionally or alternatively, the second linker, if present, (for attachment of the payload) may be present without attached payload. For example, in circumstances where the payload compound is attached by reacting with a second linker present on the nanoparticle (see, for example, doxorubicin below), the reaction may not completely saturate the available second linkers leaving some second linker "unreacted" in the nanoparticle. In certain cases, it may be advantageous that the payload does not saturate all available second linker attachment sites. For example, the present inventors have found that at high loading levels of doxorubicin (e.g. above 20, above 15 or above 9) doxorubicin molecules per nanoparticle core, aqueous solubility is diminished. Moreover, unreacted second linker (e.g. the amine linker described further herein) may itself impart advantageous properties to the nanoparticle, such as improved aqueous solubility.

For certain applications it may be desirable to have a high number and/or high proportion of liver targeting ligands, e.g. in the range 40%-90%, or 50%-80%, or 60% to 70%, where percentage represents the percentage by number of all ligands on the nanoparticle. In some cases, it may be desirable to have a low number and/or low proportion of liver targeting ligands, e.g. in the range 1%-40%, or 5%-30%, or 10% to 20%, where percentage represents the percentage by number of all ligands on the nanoparticle. In some cases the number of liver-targeting ligands (e.g. glypican-3 binding peptides as defined further herein) per nanoparticle may be around 1, 2, 3, 4, 5, 6, 7, 8, 9 or 10. In particular cases a greater number of liver-targeting ligands (e.g. glypican-3 binding peptides as defined further herein), for example 3 or more, 4 or more, or 5 or more per nanoparticle, may enhance the degree of liver targeting of the nanoparticle of the present invention. In particular cases a lower number of liver-targeting ligands (e.g. glypican-3 binding peptides as defined further herein), for example 1 or 2 per nanoparticle, may nevertheless confer sufficient liver targeting for the nanoparticle of the present invention.

For certain applications it may be desirable to have a high number and/or high proportion of payload ligands, e.g. in the range 40%-90%, or 50%-80%, or 60% to 70%, where percentage represents the percentage by number of all ligands on the nanoparticle. Where, e.g., solubility permits, having a high number or high proportion of payload allows higher concentration of payload to be delivered. In some cases, it may be desirable to have a low number and/or low proportion of payload ligands, e.g. in the range 1%-40%, or 5%-30%, or 10% to 20%, where percentage represents the percentage by number of all ligands on the nanoparticle. A lower percentage may be advantageous where, for example, stability or solubility limitations are at issue or where the potency of the payload is such that a lower concentration is both safe and effective.

For certain applications it may be desirable to have a high number and/or high proportion of dilution ligands, e.g. in the range 40%-90%, or 50%-80%, or 60% to 70%, where percentage represents the percentage by number of all ligands on the nanoparticle. In some cases, it may be desirable to have a low number and/or low proportion of dilution ligands, e.g. in the range 1%-40%, or 5%-30%, or 10% to 20%, where percentage represents the percentage by number of all ligands on the nanoparticle.

In a second aspect, the present invention provides a nanoparticle comprising:

a core comprising a metal and/or a semiconductor; and
a plurality of ligands covalently linked to the core, wherein said ligands comprise:
(i) at least one ligand of formula (I):

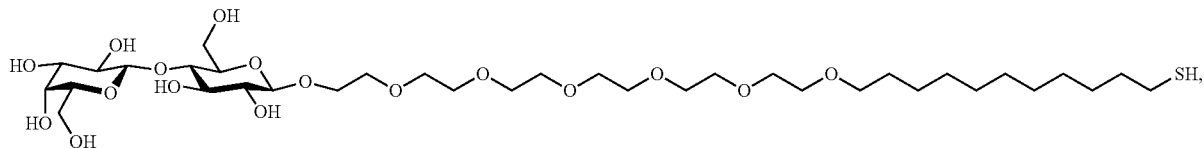

wherein the sulphur atom of the terminal thiol is bonded to the core; and
  (ii) at least one payload ligand comprising a bioactive agent; and
  (iii) optionally, at least one dilution ligand.

In accordance with the second aspect of the present invention, the payload ligand may be as defined in connection with the first aspect of the invention.

In cases in accordance with the second aspect of the invention in which said at least one dilution ligand is present, the dilution ligand may be as defined in connection with the first aspect of the invention.

In accordance with the first, second and other aspects of the present invention the core may in some cases comprise a metal selected from the group consisting of: Au, Ag, Cu, Pt, Pd, Fe, Co, Gd and Zn, or any combination thereof. In particular, the core may comprise gold.

In some cases, the diameter of the core may be in the range 1 nm to 5 nm.

In some cases, the diameter of the nanoparticle including its ligands is in the range 3 nm to 50 nm.

In some cases, the nanoparticle may comprise at least 5, 10, 20 or at least 50 ligands per nanoparticle core.

In a third aspect, the present invention provides a pharmaceutical composition comprising a plurality of nanoparticles in accordance with the first or second aspect of the invention and at least one pharmaceutically acceptable carrier or diluent.

In some cases, the pharmaceutical composition may be a sustained release formulation in which at least a portion of the plurality of nanoparticles are encapsulated in a biocompatible polymer. In particular, the biocompatible polymer may comprise poly(D,L-lactide) and/or poly(D,L-lactide-co-glycolide).

In some cases, the pharmaceutical composition may be in the form of form of a microparticle, a microsphere, a bead or a film.

In some cases, the pharmaceutical composition may be in injectable form, e.g. a depot injection.

In some cases, the pharmaceutical composition may be in concentrated form, whereby the composition may be diluted or reconstituted prior to (e.g. immediately prior to) administration to a subject.

In a fourth aspect the present invention provides a nanoparticle in accordance with the first or second aspect of the invention or a pharmaceutical composition in accordance with the third aspect of the invention for use in medicine.

In a fifth aspect the present invention provides a nanoparticle in accordance with the first or second aspect of the invention or a pharmaceutical composition in accordance with the third aspect of the invention for use in the treatment of a liver disorder in a mammalian subject.

In accordance with the present invention the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human.

In some cases, the liver disorder comprises a primary cancer of the liver or a secondary cancer of the liver (i.e. a metastatic cancer of non-liver origin that has invaded the liver).

In some cases, the liver disorder is hepatocellular carcinoma (HCC).

In some cases, the liver disorder is a cancer selected from: heptoblastoma, cholangiocarcinoma, cholangiocellular cystadenocarcinoma, angiosarcoma, hemangioendothelioma, embryonal sarcoma, fibrosarcoma, leiomyosarcoma and rhabdomyosarcoma.

In a sixth aspect, the present invention provides a method of treating a liver disorder in a mammalian subject, comprising administering a nanoparticle in accordance with the first or second aspect of the invention or a pharmaceutical composition in accordance with the third aspect of the invention to the subject in need of therapy. The liver disorder may be as defined in connection with the fifth aspect of the invention.

In a seventh aspect, the present invention provides use of a nanoparticle in accordance with the first or second aspect of the invention or a pharmaceutical composition in accordance with the third aspect of the invention in the preparation of a medicament for use in a method in accordance with the sixth aspect of the invention.

In an eight aspect, the present invention provides an article of manufacture comprising:
  a nanoparticle in accordance with the first or second aspect of the invention or a pharmaceutical composition in accordance with the third aspect of the invention;
  a container for housing the nanoparticle or pharmaceutical composition; and
  an insert or label.

In some cases, the insert and/or label provides instructions, dosage and/or administration information relating to the use of the nanoparticle or pharmaceutical composition in the treatment of a liver disorder in a mammalian subject. The liver disorder may be as defined in connection with the fifth aspect of the invention.

In a ninth aspect, the present invention provides a process for producing a nanoparticle in accordance with the first aspect of the invention, the process comprising:
  combining:
    a solution comprising sulphur containing liver targeting ligand and/or first linker;
    a solution comprising sulphur-containing second linker;
    a solution comprising a carbohydrate-linker-thiol or a carbohydrate-linker-S-S-linker-carbohydrate;

a solution comprising a core-forming metal salt; and
a reducing agent,
thereby causing the nanoparticle to self-assemble, and reacting at least one payload compound to the second linker, thereby causing the at least one payload compound to become covalently linked to the nanoparticle via said second linker;
and optionally reacting at least one liver targeting compound with said first linker causing the at least one liver targeting compound to become covalently linked to the nanoparticle via said first linker.

Suitably, the solution comprises sulphur-containing liver targeting ligand, for example, the solution may comprise a ligand of formula (I):

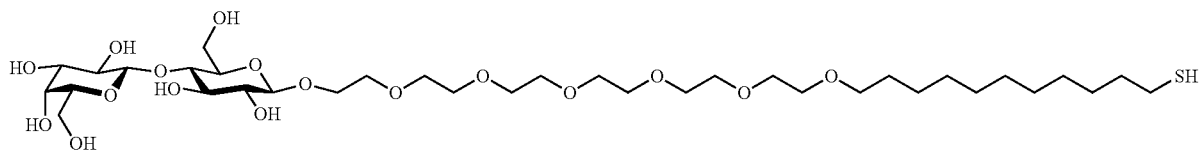

In some cases, the payload comprises doxorubicin or maytansinoid DM4.

In some cases, the carbohydrate comprises glucose or galactose.

In some cases, the core-forming metal salt comprises a gold salt.

In some cases, the reducing agent comprises sodium borohydride.

The first and/or second linkers may be functionalised to facilitate coupling of the payload. For example, a terminal ω-amino functionality may be primed for amide bond formation using known peptide coupling reagents such as EDC. The payload may be coupled to the second linker via an intermediate linker. The intermediate linker may be first coupled to the bioactive/detectable, and then coupled to the second linker, or the second linker may be functionalised with an intermediate linker to which the bioactive/detectable is coupled. For example, platinum-centred bioactive moieties may be first coupled to a succinate moiety and then coupled to the second linker using amide coupling techniques. For example, doxorubicin may be coupled to a succinate-second linker moiety.

In some cases, the method includes the step of reacting at least one detectable compound with said first linker or said second linker, causing the at least one liver targeting compound to become covalently linked to the nanoparticle via said first or said second linker.

In a tenth aspect, the present invention provides a nanoparticle in accordance with the first or second aspect of the invention or a pharmaceutical composition in accordance with the third aspect of the invention for use in a method of imaging a liver tumour, wherein said at least one payload ligand comprises a detectable agent. In particular, the detectable agent may be a fluorescent agent. In some cases, the method of imaging is a method of delineating tumour margins during surgical resection.

In an eleventh aspect, the present invention provides a method of imaging a liver tumour, comprising
administering a nanoparticle in accordance with the first or second aspect of the invention or a pharmaceutical composition in accordance with the third aspect of the invention to a subject having, or suspected of having, a liver tumour, wherein said at least one payload comprises a detectable agent; and
detecting said detectable agent, thereby delimiting or forming an image or all or a part of said liver tumour. In some cases, the detectable agent may be a fluorescent agent. In some cases, the method is for delineating tumour margins during surgical resection.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

In describing the present invention, the following terms will be employed, and are intended to be defined as indicated below.

Liver-Targeting Ligands

The liver-targeting ligand binds, couples to or interacts with a receptor, marker, protein or antigen present at, in or on liver cells (in some cases healthy liver cells, in other cases only or predominantly cancer cells of a liver tumour, e.g. hepatocellular carcinoma, in yet other cases present at, in or on both healthy liver cells and cancer cells of a liver tumour). In binding or otherwise being attracted to the liver (or a tumour thereof), the liver-targeting ligand assists with targeting the nanoparticle of the invention to the site of intended action. The liver-targeting ligand is covalently linked to the nanoparticle core (directly or more commonly via a linker) and therefore acts to cause the nanoparticle, including its payload, to associate with or otherwise come into contact with the liver (or a tumour thereof) with greater frequency, for longer duration and/or at higher concentration than would be the case for the nanoparticle in the absence of the liver-targeting ligand.

Examples of liver-targeting ligands include: lactose, FGF-4 (fibroblast growth factor 4), c-Met (hepatocyte growth factor receptor), a glypican-3 binding agent (e.g. a glypican-3 binding peptide as disclosed in U.S. Pat. No. 8,388,937 (including specifically the peptides of SEQ ID NOs: 1, 2, 3, 4, 5, 6, 7 and 10 therein, which are expressly incorporated herein by reference) or an anti-glypican-3 antibody), an alpha-fetoprotein (AFP) receptor binding agent (e.g. an AFP receptor binding peptide as disclosed in US2012/0270238 or an anti-AFP receptor antibody), and an ASGPR binding agent (e.g. galactose, N-acetylgalactosamine, lactose, glucose, mannose, or a glycomimetic ligand such as disclosed in Mamidyala et al., *J. Am. Chem. Soc.*, 2012, Vol. 1334, No. 4, pp. 1978-1981). The liver-targeting ligand may also be an antibody or binding fragment thereof, e.g. a Fab fragment (fragment antigen-binding), single domain antibody/nanobody directed at a liver or hepatocyte target such as glypican-3, ASGPR, FGF-4, c-Met, AFP or other liver-expressed protein or liver-expressed receptor.

Figure 1A:
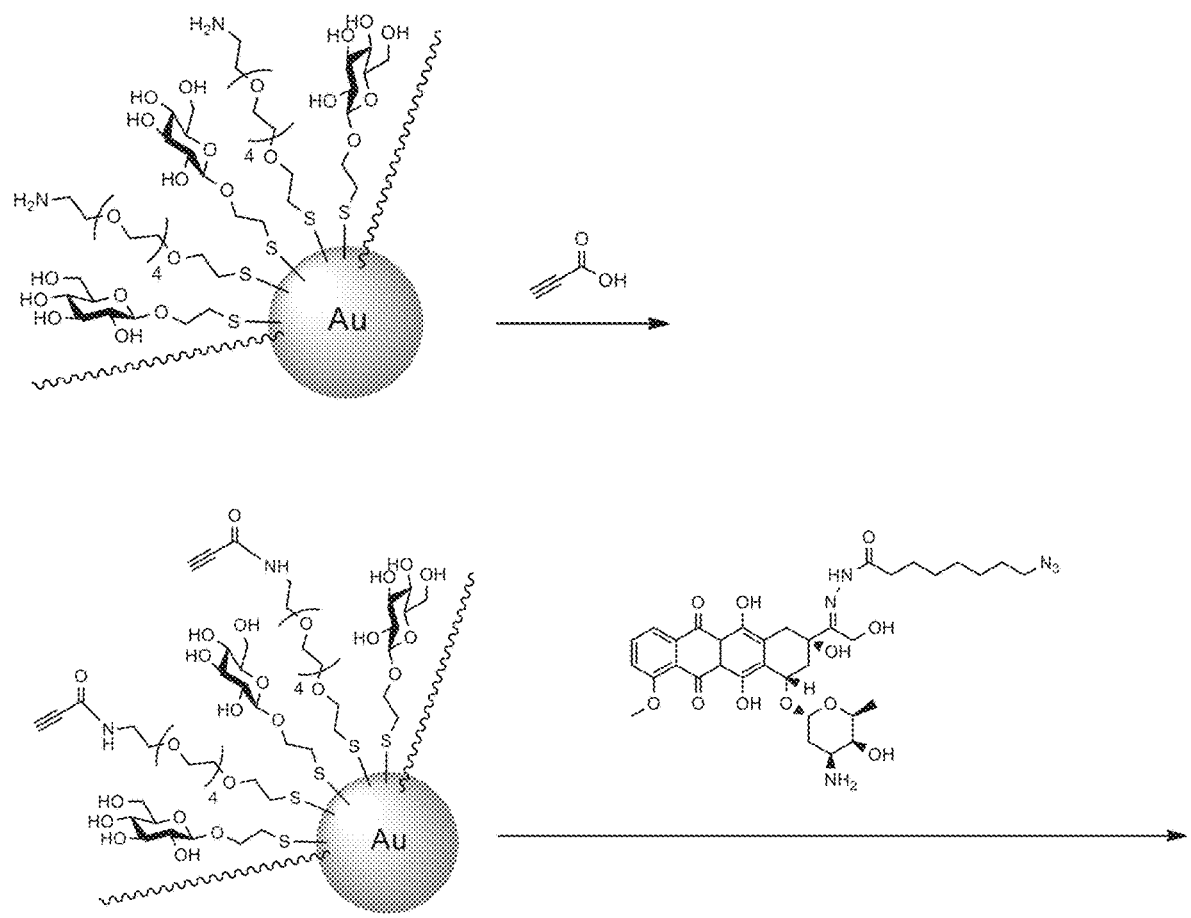
FIG. 1A shows an overview of the general "click chemistry" reaction scheme.
Figure 1:
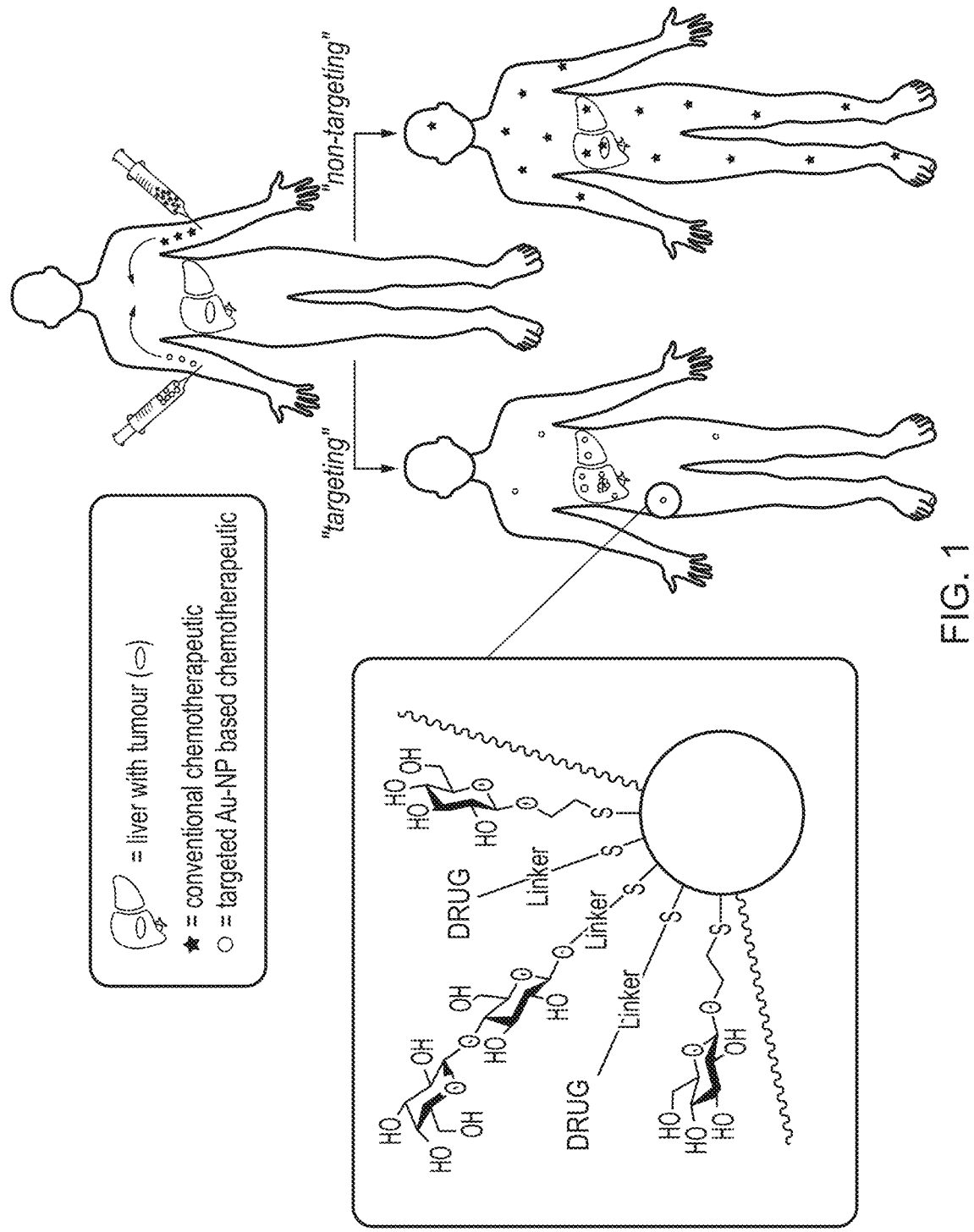
FIG. 1 shows a schematic and simplified depiction of biodistribution for conventional chemotherapeutics and liver-targeted nanoparticles.
Figure 2:
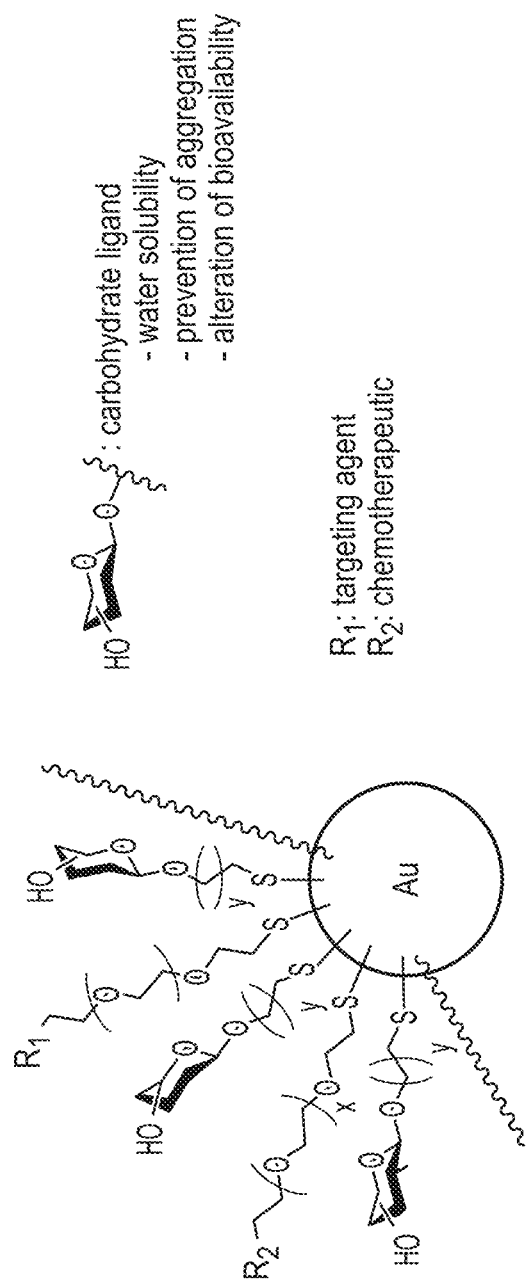
FIG. 2 shows a schematic depiction of a functionalised gold nanoparticle with carbohydrate (dilution) ligands, targeting agent ($R_1$) containing ligands and chemotherapeutic ($R_2$) containing ligands. Repeating ethylene glycol and alkyl groups are indicated by the subscripts x and y, respectively.

The asialoglycoprotein receptor (ASGPR) is believed to be a suitable target for targeting payload-carrying nanoparticles to the liver. ASGPR recognises galactose residues and is expressed in the liver and not in other human tissues. The combined attachment of targeting agents (such as lactose) and chemotherapeutic to an ultra-small glyco-coated gold nanoparticle (1.6-1.8 nm) provides unique properties for the treatment of HCC. After administration and circulation in the body the targeted Au-NPs accumulate in the liver and ASPGR overexpressing HCC (FIG. 1, "targeting"), whereas a conventional chemotherapeutic is widely distributed (FIG. 1, "non-targeting"). Furthermore, the small Au-NPs (<2 nm) show increased tumour penetration potential compared to larger NPs (~15 nm) and provide a beneficial surface coverage (Huang, K. et al., *ACS Nano*, 2012, Vol. 6, pp. 4483-4493; Kumara, C. et al., *ACS Nano*, 2014, Vol. 8, pp. 6431-6439). A schematic of such a functionalised gold nanoparticle is shown in FIG. 2.

The ligand corona exhibits meta stability under physiological conditions due to the Au-sulphur bond, stable in plasma and released in the cytosol. Here, we present promising results of a targeted GNP chemotherapeutic screening study utilising in vitro, ex vivo and in vivo model towards efficient liver targeting.

Glypican-3 binding peptides include RLNVGGTYFLTTRQ (SEQ ID NO: 1), YFLTTRQ (SEQ ID NO: 2) and variants thereof differing from said sequence by addition, deletion, substitution or chemical modification (e.g. unnatural or modified amino acids) of not more than 3, not more than 2 or not more than 1 amino acid. Said variants may for example comprise one, two or three unnatural or modified amino acids. Suitable unnatural amino acids include, for example, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of natural amino acids, such as trifluorotyrosine, p-Cl-phenylalanine, p-Br-phenylalanine, p-I-phenylalanine, L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine—such as 1-methyl-Phe, pentamethyl-Phe, L-Phe(4-amino), L-Tyr(methyl), L-Phe(4-isopropyl), L-Tic(1,2,3,4-tetrahydroisoquinoline-3-carboxyl acid), L-diaminopropionic acid and L-Phe(4-benzyl). The peptides may be further modified. For example, one or more amide bonds may be replaced by ester or alkyl backbone bonds. There may be N or C alkyl substituents, side chain modifications or constraints such as disulphide bridges, side chain amide or ester linkages. The variant peptides may include both modified peptides and synthetic peptide analogues. Peptides may be, for example, be modified to improve solubility, formulation and storage properties, or to protect labile peptide bonds by incorporating non-peptidic structures.

It is specifically contemplated herein that the N-terminus and/or C-terminus of a peptide, such as a glypican-3 binding peptide, may be modified by N-terminal acetylation and/or C-terminal amidation. In particular, such terminal modification(s) may assist with the covalent attachment of the liver-targeting peptide to the nanoparticle (e.g. via a linker).

Nanoparticles

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry. References to "diameter" of a nanoparticle or a nanoparticle core a generally taken to mean the longest dimension of the nanoparticle or nanoparticle core, respectively. For nanoparticles having a substantially polyhedral or spherical geometry, the shortest dimension across the particle will typically be within 50% of the longest dimension across the particle and may be, e.g., within 25% or 10%.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention.

As used herein, "corona" refers to a layer or coating, which may partially or completely cover the exposed surface of the nanoparticle core. The corona includes a plurality of ligands covalently attached to the core of the nanoparticle. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the core. In certain cases the corona facilitates solubility, such as water solubility, of the nanoparticles of the present invention.

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 50 nm, more preferably between 3 and 10 nm and most preferably between 4 and 5 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometre range. Other particularly useful core materials are doped with one or more atoms that are NMR active, allowing the nanoparticles to be detected using NMR, both in vitro and in vivo. Examples of NMR active atoms include $Mn^{-2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots.

Nanoparticle cores comprising semiconductor compounds can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamines or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{37}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$ The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Actives

As used herein the term "biologically active agent" or "bioactive agent" is intended to encompass drugs and pro-drugs that exert an effect on a biological system, preferably a therapeutic effect. Class of active agent contemplated herein include small molecule organic compounds, peptides, polypeptides and nucleic acids. An exemplary class of therapeutic agent is an anti-cancer agent, such as a cytotoxic compound, an anti-proliferative agent or an anti-angiogenic agent. Particular examples include chemotherapeutic agents, e.g. doxorubicin, temozolomide, irinotecan, carmustine, platinum(IV), platinum(II), camptothecin, docetaxel, sorafenib, maytansine, a maytansinoid (e.g. maytansinoid DM1 or maytansinoid DM4), monomethyl auristatin E (MMAE) and a histone deacetylase (HDAC) inhibitor (e.g. panobinostat).

In certain cases, the at least one payload ligand is selected from:

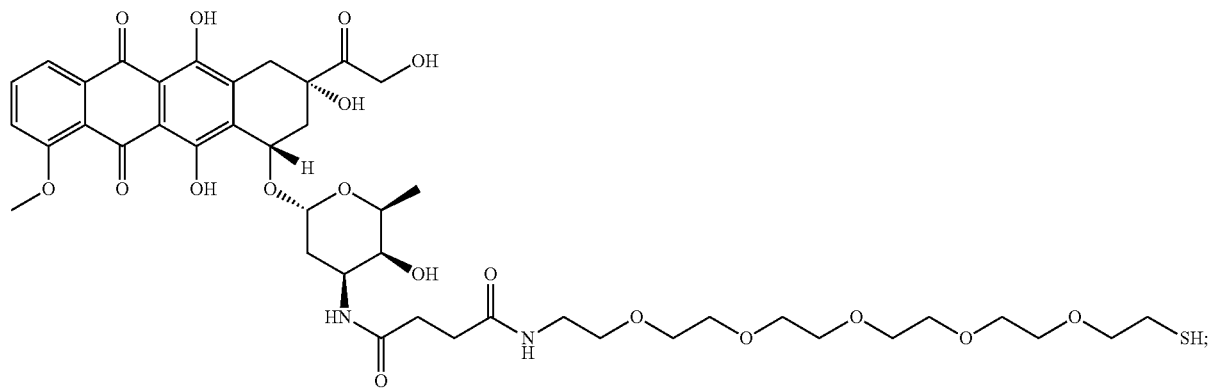
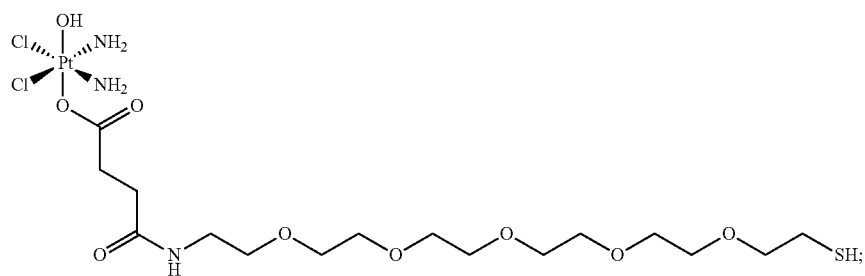
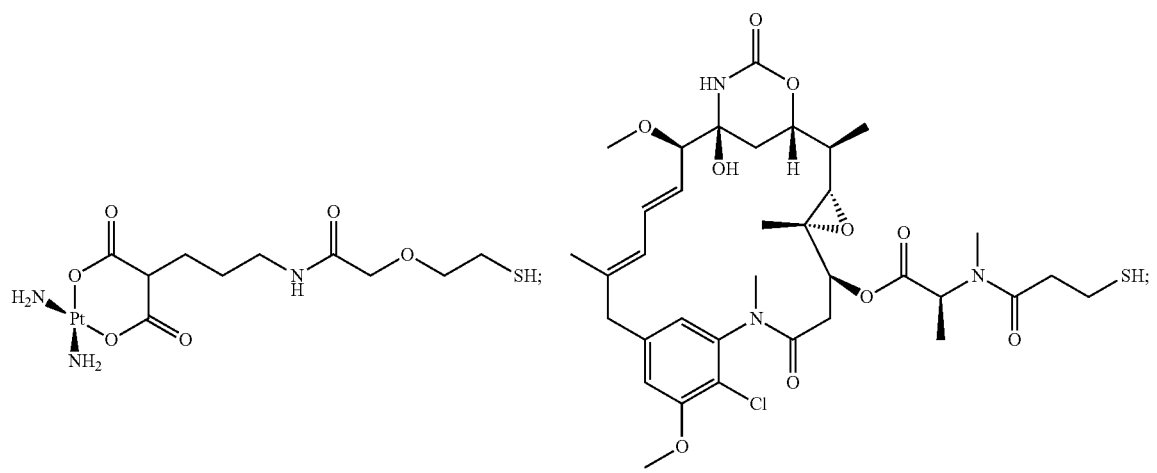
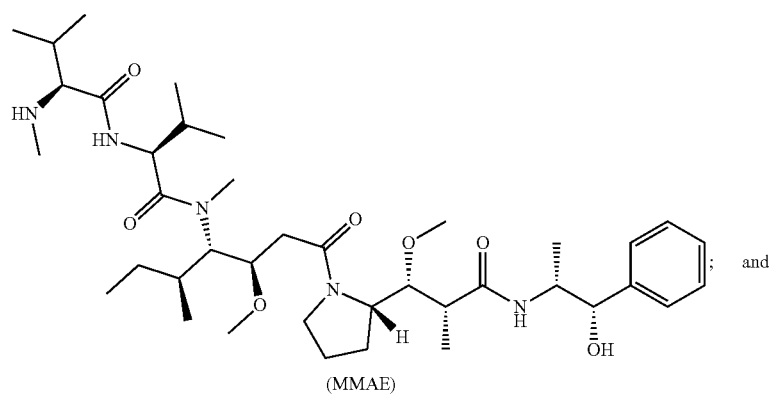
(MMAE)
; and

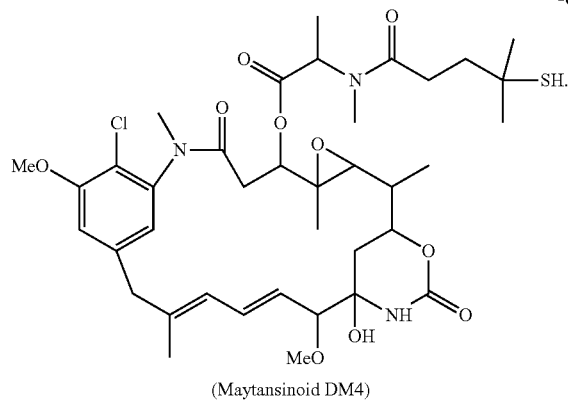

(Maytansinoid DM4)

Detectable Agents

Detectable agents include fluorescent label and opto-acoustics dyes. Examples of both are known in the art. Without limitation, examples of fluorescent dyes include rhodamines dyes (such as rhodamine B and sulforhodamine B) and Cy5.5. Without limitation, examples of opto-acoustic dyes include Cy7, Cy7.5, Cy8, or Li-cor® IRDye800®.

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, including depot injection.

The nanoparticles of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution or liquid which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g., intravenous injection.

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, New York, USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight. One benefit of the liver targeting of the nanoparticles of the present invention is that a therapeutically effective dose of the active "payload" may be lower in comparison with the effective dose of the same active when administered as a free drug, e.g., by systematic administration.

The following is presented by way of example and is not to be construed as a limitation to the scope of the claims.

EXAMPLES

Syntheses of Exemplary Ligands and Linkers
Lactose Long Linker Ligand

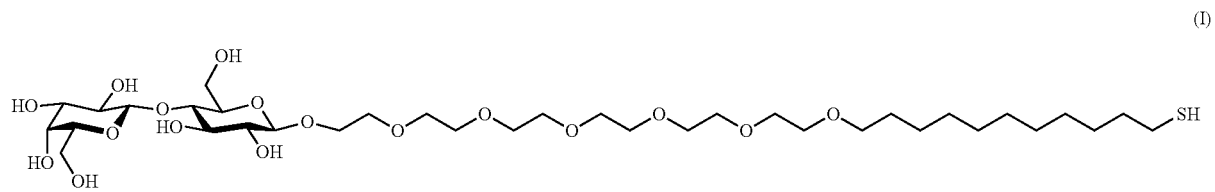
(I)

Also referred to as Lac-O-EG$_6$-C$_{11}$-SH and LacLL, this ligand+linker moiety has the IUPAC name ω-11-Thioundecyl)-hexaethylene glycolyl β-D-lactoside. It may be synthesised according to A. G. Barrientos, J. M. de la Fuente, T. C. Rojas, A. Fernandez, S. Penades, *Chem. Eur. J.* 2003, 9, 1909-1921.

Glucose Short Linker (Dilution Ligand)

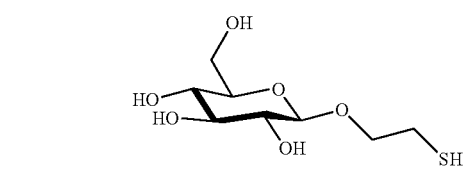

Also referred to Glc-C2-SH, GlcSL, GlcC2, this ligand has the IUPAC name thioethyl β-D-glucopyranoside. It may be synthesised according to Midatech Patent WO 2006/037979 A2 and R. Ojeda, J. L. de Paz, A. G. Barrientos, M. Martin-Lomas, S. Penades, *Carbohydr. Res.* 2007, 342, 448-459.

Amino Linker

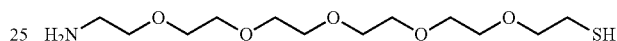

Often referred to the amino linker, this linker is also abbreviated to AL and NH$_2$-EG$_6$-SH. Its IUPAC name is α-amino-ω-thiohexaethylene glycol. It may be synthesised and isolated as the corresponding disulphide from hexaethylene glycol as follows:

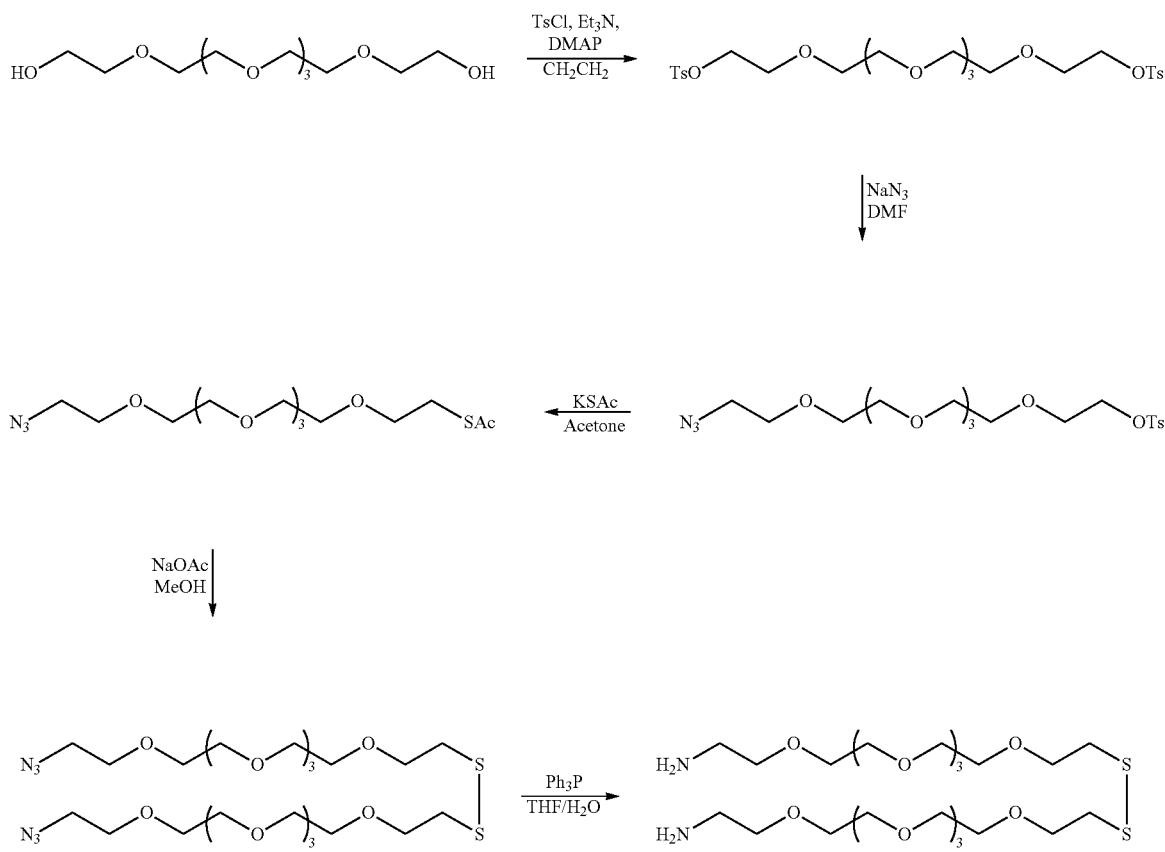

The following representative procedures are described. Hexaetylene glycol (90.0 g, 318.8 mmol) was dissolved in dichloromethane (1 l) and trimethylamine (177 mL, 1275 mmol) and DMAP (1.94 g, 15.9 mmol) were added. The mixture was cooled to 4° C. and tosyl chloride (181.8 g, 956.3 mmol) was added portion wise over 30 minutes. After 10 minutes at around 5° C., the reaction was allowed to warm to room temperature and stirred for 3 hours, then poured into a solution of ethylenediamine in dichloromethane (23.0 ml 344.4 mmol in 630 mL). The organic layer was washed (HCl, 630 ml, 5%; NaHCO$_3$, 5%; brine, each 630 mL), dried over Na$_2$SO$_4$ and concentrated in vacuo to give 217.69 g product which was used without further purification.

This product was dissolved in dimethylformamide (1.4 l) and sodium azide (24.9 g, 382.5 mmol) was added. The reaction was stirred under argon at room temperature for 18 h, then poured into brine (1300 ml) and extracted with ethyl acetate (2×630 ml). The extracts were dried (Na$_2$SO$_4$), concentrated in vacuo and purified (chromatography, SiO$_2$, 15-40% acetone/hexanes) to afford 62.67 g (42%) tosyl azide.

This tosyl azide was dissolved in acetone (630 ml) and potassium thioacetate (20.2 g, 176.5 g) was added. After 19 h, the reaction mixture was poured into brine (1.2 l) and extracted with ethyl acetate (3×600 ml). The extracts were dried (Na$_2$SO$_4$), concentrated and purified (chromatography, SiO$_2$, 0-4% methanol/dichloromethane) to afford 46.1 g thioacetyl azide (93%).

This thioacetyl azide was discolved in methanol (1.1 l) and sodium methoxide (68.1 g, 1261.5 mmol) was added portion wise. The reaction was stirred (open to the air) for 5 days, then diluted with water (700 ml) and extracted with dichloromethane (2×700 ml). The extracts were dried (Na$_2$SO$_4$), concentrated and purified (chromatography, SiO$_2$, 40% acetone/hexanes) to afford 22.3 g of disulfide (55%).

This disulfide was dissolved in tetrahydrofuran (225 ml) and water (70 ml) and triphenylphosphine (18.6 g, 71.0 mmol) were added. The reaction mixture was stirred at room temperature under argon for 16 h, then diluted with water (50 ml) and washed with ethyl acetate (3×100 ml). The resultant aqueous solution was concentrated in vacuo to afford 11.3 g of amino linker.

Example 1—Synthesis of Liver Targeting Lactose Long Linker Gold Nanoparticles

The preparation and characterisation of gold nanoparticles loaded with a liver targeting molecule, an attachment linker and a carbohydrate diluent attached to the gold surface is described below.

The ligands LacLL, AL and GlcC2 were used. A hexaethylene glycolyl undecanyl lactose glycoside was chosen as liver targeting moiety while a shorter C2 glucoside was utilised as a diluent moiety. For the attachment of chemotherapeutic pay-loads or other therapeutic or diagnostic molecules like drugs, fluorescent dyes and radio tracer an amino functionalised hexaethylene glycol was used. The coupling to the gold core was realised via a gold sulfur bond.

Figure 3A:
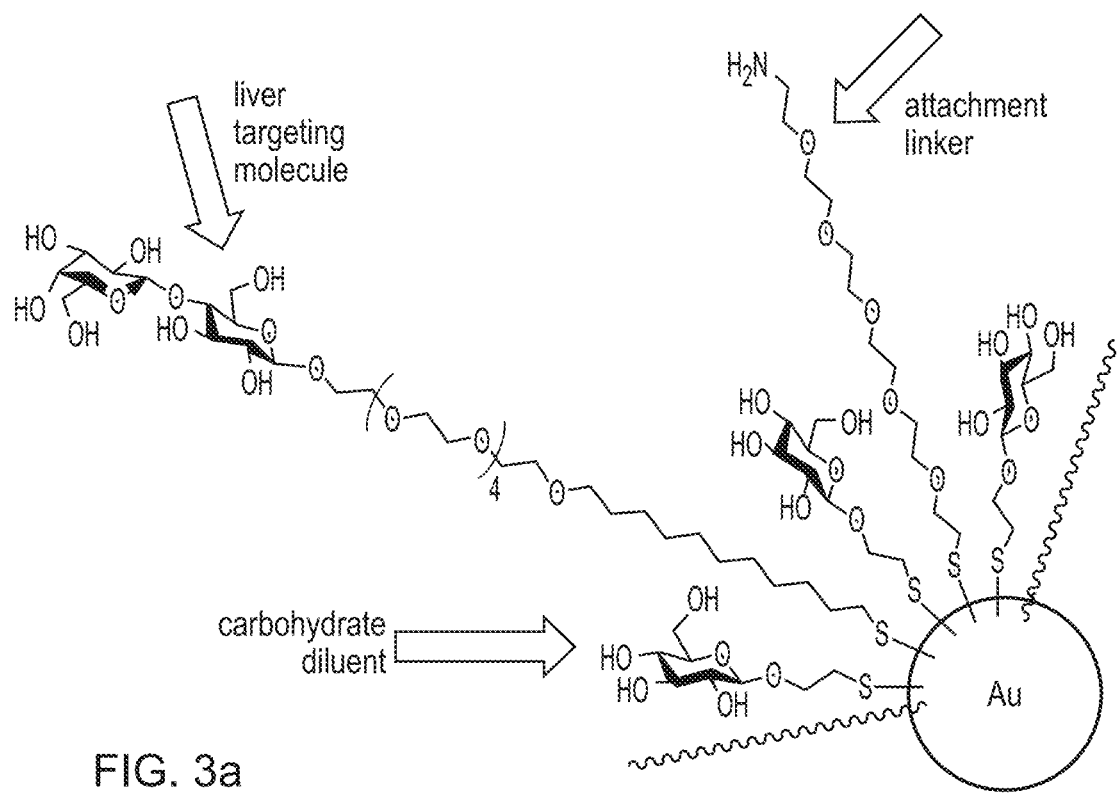
FIG. 3 shows schematic depictions of a LacLL-NP without a payload (a) and the corresponding Pt-LacLL-NP (b) with a Pt-succinate payload.
Figure 4A:
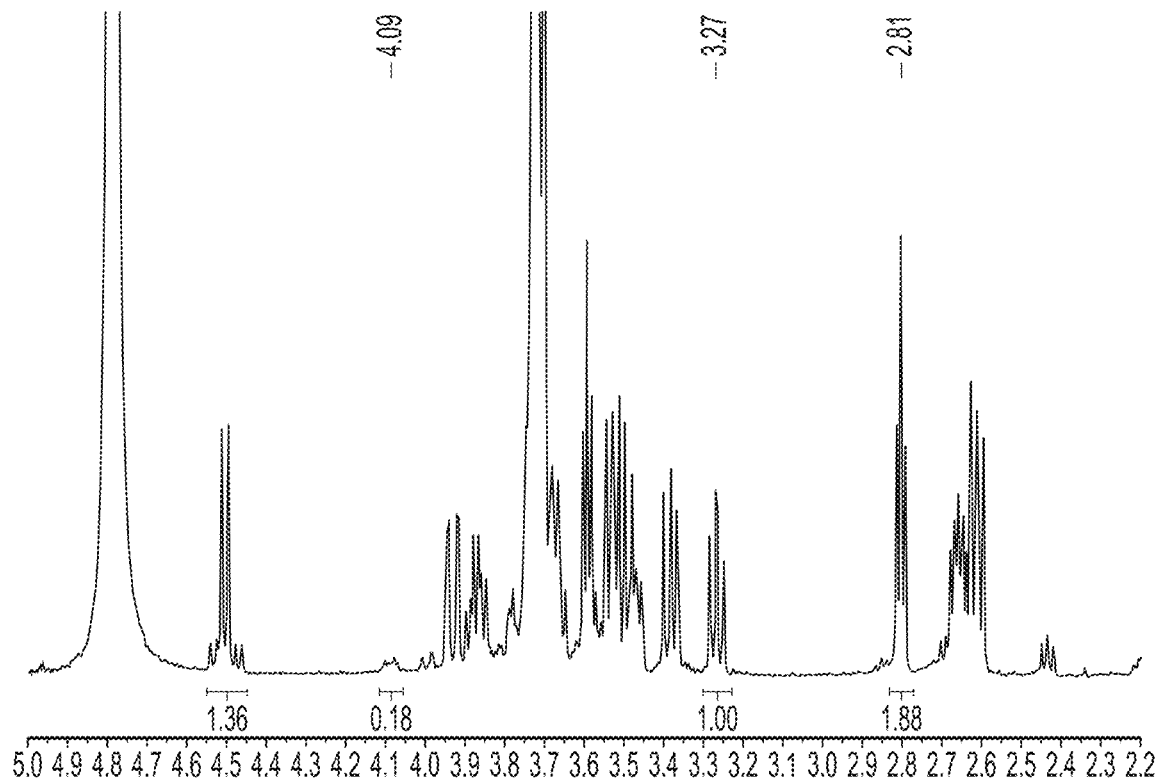
FIG. 4 shows the H NMR spectra of the nanoparticles of FIG. 3 after KCN etching. (a) shows the spectrum of LacLL-NP1 after KCN etching. Report signals: LacLL=4.09 ppm, AL=2.81 ppm, GlcC2=3.27 ppm; (b) shows the spectrum of Pt-LacLL-NP3 after KCN etching. Report signals: Pt(IV)-suc=2.47 ppm, LacLL=4.08 ppm, AL=2.79 ppm, GlcC2=3.26 ppm.
Figure 5:
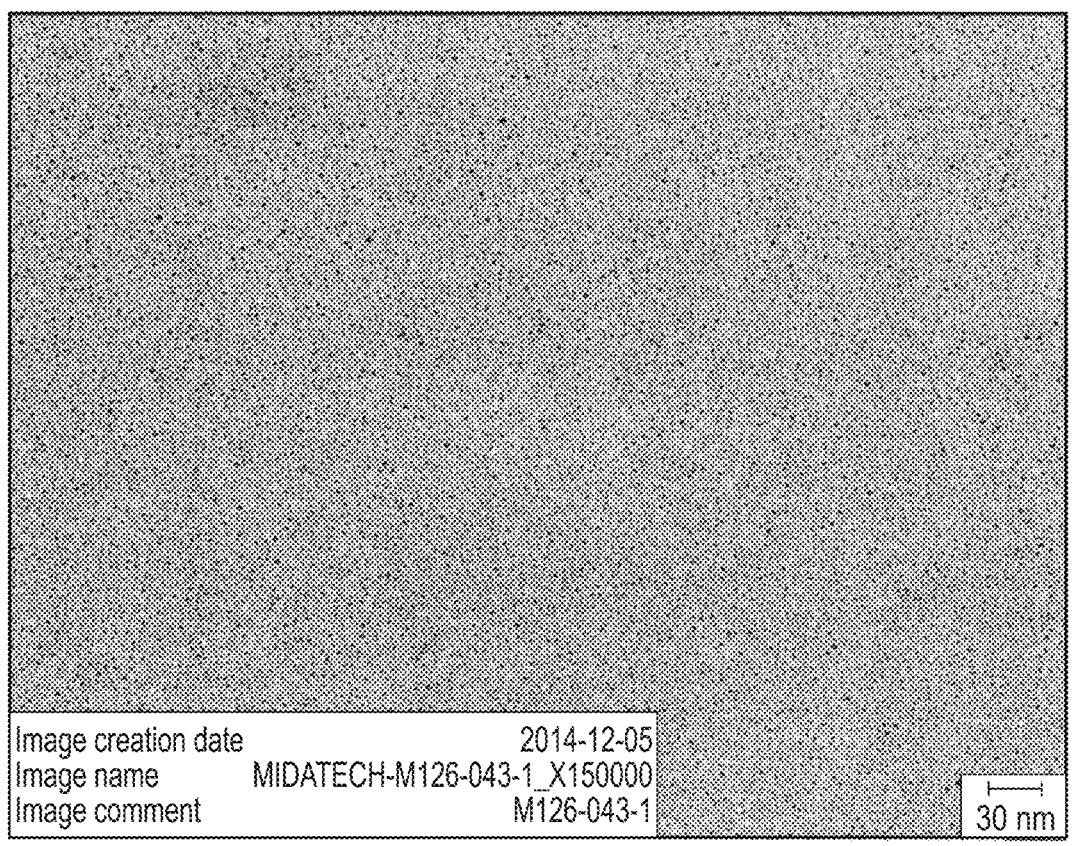
FIG. 5 shows TEM images and data for LacLL-NP1.
Figure 5:
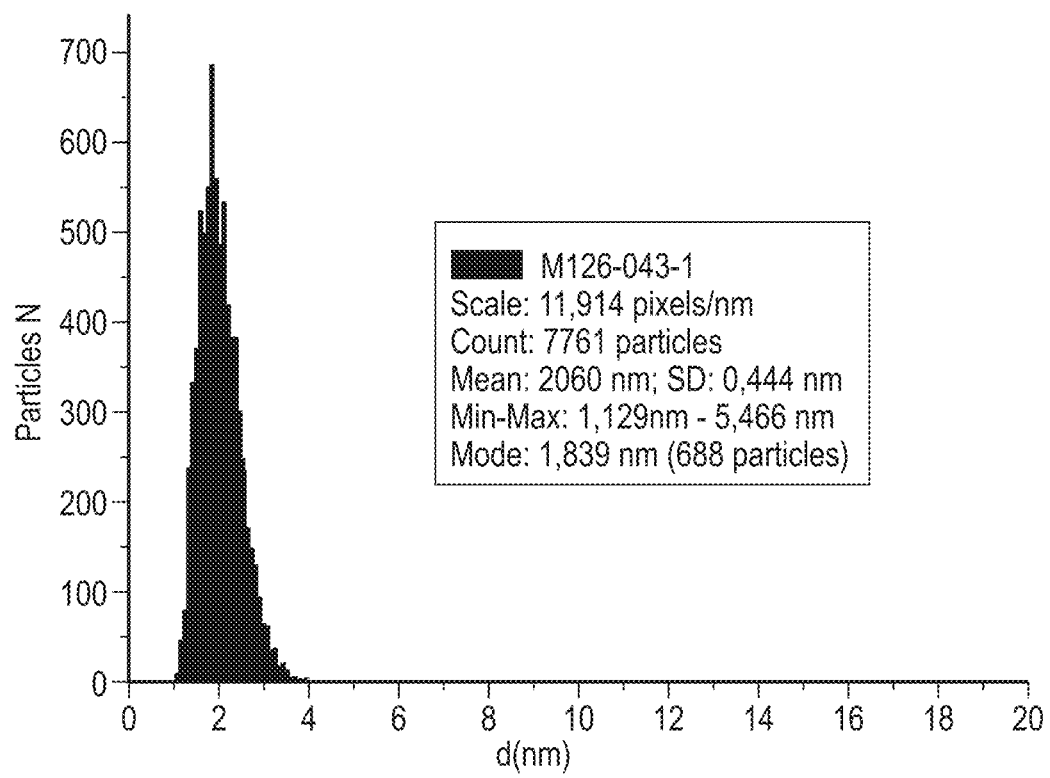

Gold nanoparticles with different ratios of the liver targeting molecule LacLL were synthesized: LacLL-NP1 (LacLL:AL:GlcC2 9:50:41) and LacLL-NP2 (LacLL:AL:GlcC2–27:50:23). For the preparation of the nanoparticles the ligands LacLL, AL and GlcC2 were dissolved in methanol in the desired proportions and added to a solution of HAuCl$_4$ in water. The gold salt was reduced in the present of thiols/disulfides to gold(0) clusters with a ligand corona. After purification by repeated centrifuge filtration and final dilution to the desired volume nanoparticles were obtained as aqueous solutions (FIG. 3A). The ligand ratio on the nanoparticle was confirmed by $^1$H NMR. Therefore, an aliquot of the nanoparticle solution was treatment with 0.3 m KCN and 0.1 m KOH in deuterated water after solvent exchange to D$_2$O. After etching of the gold core the spectra of free ligands was acquired and the ligand ratio was determined by report signal integration indicating that the original ratio was maintained on nanoparticles after reaction in the range of error (FIG. 4A). The mean diameters of these constructs, determined using transmission electron microscopy (TEM), were 2.06 nm and 1.98 nm for LacLL-NP1 and LacLL-NP2 (FIG. 5 shows the TEM of LacLL-NP1).

Experimental Section

LAcLL, AL and GlcC2 were synthesized according to references. HAuCl$_4$, NaBH$_4$, KCN, KOH and methanol were purchased from Sigma-Aldrich. All reagents were used without further purification. MilliQ water (18.2 mΩ) was obtained from Simplicity water purification system (Merck Millipore). The nanoparticles were characterized by $^1$H NMR after KCN/KOH etching, DLS, TEM and zeta potential. The gold concentration of the nanoparticle solution was determined by ICP-MS or MPAES.

For the NMR sample preparation 1 mL solution of the nanoparticles was concentrated and washed (3×2 mL D$_2$O) by centrifuge filtration (Amicon, 10 kDa, 4 mL). The residual NP solution (~200 μL) was incubated with a solution of 0.3 m KCN/0.1 m KOH in D$_2$O (~400 μL) for 30 minutes at 50° C. The mixture was shortly spun and the supernatant was transferred to a NMR tube. $^1$H NMR spectra were recorded on a Bruker AVANCE III 500 NMR spectrometer. Chemical shifts were calibrated to the corresponding solvent (D$_2$O=4.79 ppm).

a) LacLL-NP1 (LacLL:AL:GlcC2–9:50:41)

Methanolic solutions of LacLL (0.0410 mmol; 32.5 mg; 1.41 mL), GlcC2 (0.185 mmol; 44.5 mg; 1.58 mL) and AL (0.228 mmol; 67.7 mg; 2.40 mL) were added to 100 mL round bottom flask and diluted with methanol (32.4 mL) to obtain a concentration of 0.012 M of ligands solution. HAuCl$_4$ (60.0 mg; 0.152 mmol; 1 eq.) solution in water (6.09 mL) was then added. The reaction mixture was reduced with NaBH$_4$ (126 mg; 3.34 mmol; 22 eq.) solution in water (3.33 mL) under vortex agitation. The resulting black nanoparticle solution was shaken at room temperature for 35 minutes on an orbital shaker. Over time the nanoparticles precipitated. After finishing the reaction the in solution remaining nanoparticles were spun down by centrifugation (1 min at 4500 rpm) and the precipitate was redissolved in 4 mL of MilliQ water. The aqueous NP suspension was transferred to a previously washed AMICON filter (4 mL, 10 kDa). After concentration the nanoparticles were washed four times with MilliQ water (3-4 mL) by centrifuge filtration. Finally the nanoparticles were collected in a final volume of 6 mL MilliQ water. The nanoparticles were characterized by $^1$H NMR after KCN/KOH etching, DLS, TEM and zeta potential. The gold concentration of the nanoparticle solution was determined by ICP-MS. TEM: average diameter 2.06 nm.

b) LacLL-NP2 (LacLL:AL:GlcC2 27:50:23)

Methanolic solutions of LacLL (0.0870 mmol; 69.8 mg; 3.55 mL), GlcC2 (0.0710 mmol; 17.0 mg; 1.67 mL) and AL (0.159 mmol; 47.2 mg; 1.96 mL) were added to 100 mL round bottom flask and diluted with methanol (19.3 mL) to obtain a concentration of 0.012 M of ligands solution. HAuCl$_4$ (40.0 mg; 0.102 mmol; 1 eq) solution in water (4.24 mL) was then added. The reaction mixture was reduced with NaBH$_4$ (84.8 mg; 2.24 mmol; 22 eq) solution in water (2.33 mL) under vortex agitation. The resulting black nanoparticle solution was shaken at room temperature for 35 minutes on an orbital shaker. Over time the nanoparticles precipitated. After finishing the reaction the in solution remaining nanoparticles were spun down by centrifugation (1 min at 4500 rpm) and the precipitate was redissolved in 4 mL of MilliQ water. The aqueous NP suspension was transferred to a previously washed AMICON filter (4 mL, 10 kDa). After concentration the nanoparticles were washed four times with MilliQ water (3-4 mL) by centrifuge filtration. Finally the nanoparticles were collected in a final volume of 4 mL MilliQ water. The nanoparticles were characterized by H NMR after KCN/KOH etching, DLS, TEM and zeta potential. The gold concentration of the nanoparticle solution was determined by ICP-MS.

TEM: average diameter 1.98 nm.

Example 2—Functionalisation of Liver Targeting Lactose Long Linker Gold Nanoparticles with Different Payloads The functionalisation of the attachment linker and characterisation of liver targeting gold nanoparticles equipped with chemotherapeutics and a fluorescent dye is described below.

Figure 3B:
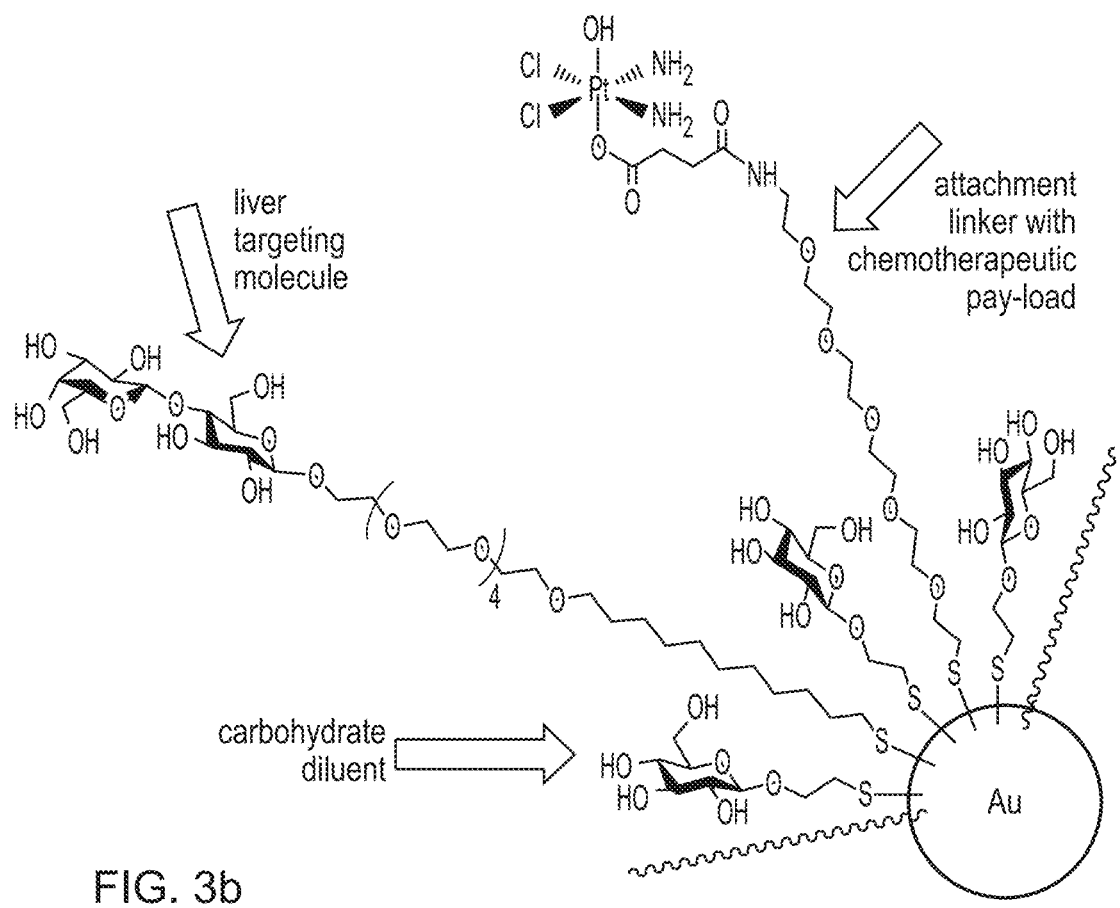
Figure 4B:
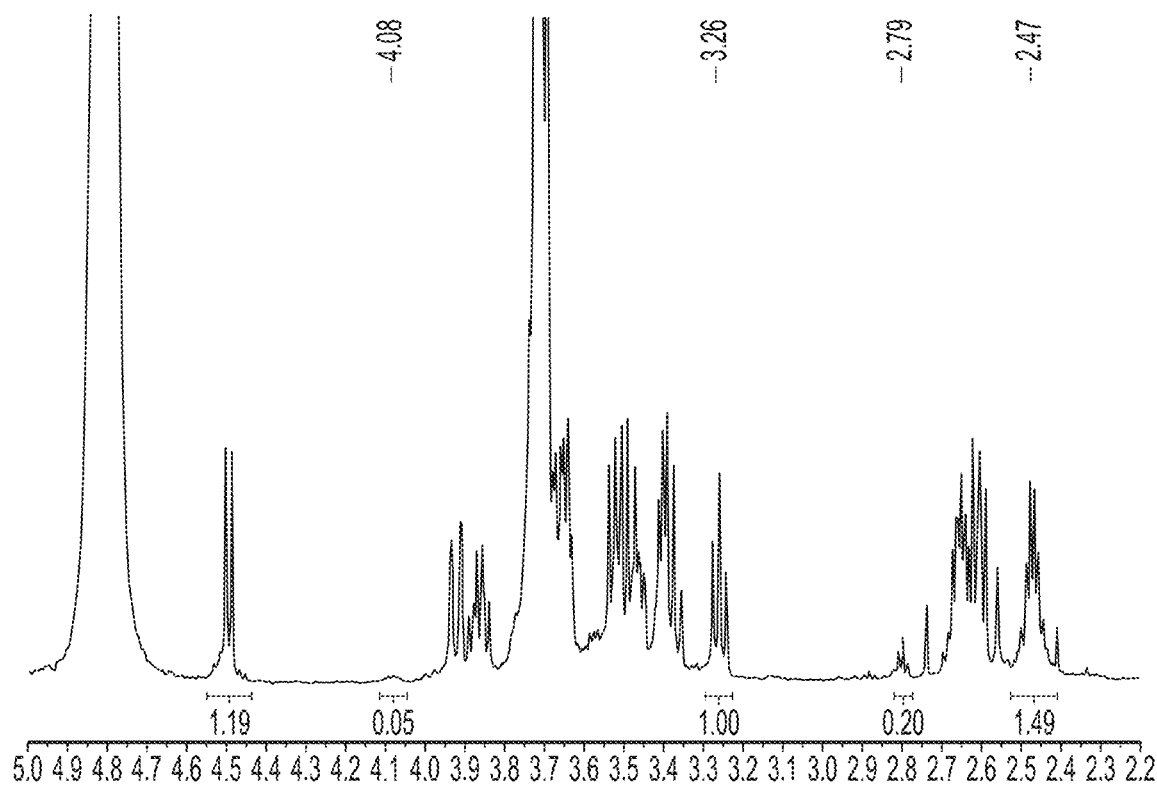

For the functionalisation of the liver targeting nanoparticles two antineoplastic agents were chosen as chemotherapeutics: platinum-(IV)-succinate (Pt(IV)-suc) and doxorubicin. Both chemotherapeutics were coupled to the attachment linker via EDC*HCl/NHS promoted amide bound formation. In the case of Pt(IV)-suc the reaction was performed in DMSO, because the compound was not soluble in aqueous systems. Therefore, the nanoparticle solution was exchanged to DMSO either via lyophilisation or centrifuge concentration and subsequent dilution. Then, the EDC*HCl/NHS pre-activated succinate was reacted with the nanoparticles overnight. Final washings to remove remaining reagents provided an aqueous solution of liver targeting gold nanoparticles with platinum based chemotherapeutic payload (FIG. 3B). The Pt/Au ratio was determined by MPAES to 1/15. The covalent attachment of the drug to the nanoparticle was shown by $^1$H NMR of the final construct after etching (FIG. 4B). The original signal of the amino methylene group with a chemical shift of 2.81 ppm virtually disappears, while a new multiplet of the succinic ethylene group at 2.47 ppm can observed in the spectrum. The integrals of the reporter signals were not changed indicating corona stability during on nanoparticle manipulations.

For the doxorubicin coupling an inverse attachment strategy was applied. First the amino function was converted to a carboxylic moiety by reaction of the LacLL-NP with succinic anhydride. The carboxylic acid was then reacted with EDC*HCl/NHS in DMSO. After solvent exchange the pre-activated nanoparticle solution was incubated with a doxorubicin solution in HEPES buffer. After purification by centrifuge filtration and final dilution in MES buffer a doxorubicin pay-loaded liver targeting nanoparticle was obtained. The gold and doxorubicin concentration was determined by a colorimetric assay.

The fluorescent dye sulfo-rhodamine B acid chloride was used as a diagnostic mimic. The coupling was realized by a sulphonamide attachment of the sulfonyl chloride moiety of the sulfo-rhodamine B acid chloride with amino function of the attachment linker on the liver targeting gold nanoparticle. The reaction was performed in carbonate buffer at pH 9.3 to obtain labelled particles.

The three experiments showed chemical flexibility for the functionalization of liver targeting gold nanoparticles.

Experimental Section

Sulfo-rhodamine B acid chloride, EDC*HCl, NHS and DMSO were purchased from Sigma-Aldrich. Pt(IV)-succinate was purchased from Charnwood Molecular. Doxorubicin was purchased from LC Labs. All reagents were used without further purification. MilliQ water (18.2 mΩ) was obtained from Simplicity water purification system (Merck Millipore). The nanoparticles were characterized by $^1$H NMR after KCN/KOH etching, DLS, TEM and zeta potential. The gold concentration of the nanoparticle solution was determined by ICP-MS or MPAES.

For the NMR sample preparation 1 mL solution of the nanoparticles was concentrated and washed (3×2 mL D$_2$O) by centrifuge filtration (Amicon, 10 kDa, 4 mL). The residual NP solution (~200 μL) was incubated with a solution of 0.3 m KCN/0.1 m KOH in D$_2$O (~400 μL) for 30 minutes at 50° C. The mixture was shortly spun and the supernatant was transferred to a NMR tube. $^1$H NMR spectra were recorded on a Bruker AVANCE III 500 NMR spectrometer. Chemical shifts were calibrated to the corresponding solvent (D$_2$O=4.79 ppm).

a) Pt-LacLL-NP3

5 mL of aqueous LacLL-NP1 nanoparticle solution (low concentration of targeting ligand) (21.4 μmol reactive AL) was concentrated by centrifugation (2×15 minutes at 4500 rpm) in an Amicon filter (4 mL, 10 kDa) and diluted to a volume of 2.5 mL with DMSO. Prior to addition to a solution of Pt(IV)-succinate (22.9 mg, 52.9 μmol) in DMSO (528 μL, 0.1 m) a solution of EDC*HCL (12.2 mg, 63.4 μmol) in DMSO (127 μL, 0.5 m) and NHS (7.29 mg, 63.4 μmol) in DMSO (63.4 μL, 1.0 m) were mixed and incubated for 15 minutes at room temperature. After 30 minutes of pre-activation the reaction mixture was added to the nanoparticle solution and the mixture was shaken on an orbital shaker at room temperature overnight. The reaction solution was diluted with 25 mL MilliQ water and concentrated and repeatedly washed with MilliQ water. The black residue was collected in 5.00 mL MilliQ water. The nanoparticles were characterized by $^1$H NMR after KCN/KOH etching, DLS, TEM and zeta potential. The gold and platinum concentration of the nanoparticle solution was determined by ICP-MS. [Au], MPAES: 2.84 mg/mL; [Pt], MPAES: 0.19 mg/mL.

b) Doxo-LacLL-NP4

Succination of amino function on LacLL-NP: 8.0 mL of aqueous LacLL-NP1 nanoparticle solution (low concentration of targeting ligand) (33.8 μmol reactive AL) was concentrated by centrifugation (15 minutes at 4500 rpm) in an Amicon filter (15 mL, 10 kDa) and diluted to a volume of 8.0 mL with DMSO. Succinic anhydride (16.9 mg, 169 μmol) was dissolved in DMSO (564 μL) to obtain a 0.5 m solution and added to the nanoparticle solution. The reaction mixture was shaken on an orbital shaker at room temperature overnight. The reaction solution was diluted with 25 mL MilliQ water and concentrated and repeatedly washed with MilliQ water. The black residue was collected in 5.00 mL MilliQ water. The nanoparticles were characterized by $^1$H NMR after KCN/KOH etching, DLS, TEM and zeta potential. The gold and platinum concentration of the nanoparticle solution was determined by ICP-MS.

Doxorubicin attachment to succinated attachment linker of LacLL-NP: 3.0 mL of aqueous LacLL-NP nanoparticle solution (10.0 µmol reactive succinated AL) was concentrated by centrifugation (15 minutes at 4500 rpm) in an Amicon filter (4 mL, 10 kDa) and diluted to a volume of 3.0 mL with DMSO. A solution of EDC*HCl (4.82 mg, 25.1 µmol) and (5.75 mg, 50.0 µmol) in DMSO (416 µL) which was incubated for 15 minutes was added to the nanoparticle solution and the mixture was shaken for 2 hours at room temperature on an orbital shaker. The nanoparticle solution was diluted with water (80 mL) was filtered by centrifugation, diluted with HEPES buffer (pH 7.8, 25.0 mL) and a solution of doxorubicin (2.50 mL, 2.00 mg/mL in HEPES 20 mM) was added immediately. The coupling reaction was incubated at room temperature for 1 hour. The nanoparticles coupled with DOX were purified with MilliQ water by centrifuge filtration (Amicon, 15 mL, 10 kDa). The residual solution was collected in MES buffer (3.0 mL). The nanoparticles were characterized by $^1$H NMR after KCN/KOH etching, DLS, TEM and zeta potential. The gold concentration of the nanoparticle solution was determined by ICP-MS. [Au], colorimetric: 1.05 mg/mL; [Doxo], colorimetric: 0.66 mg/mL.

c) sRhoB-LacLL-NP5

3 mL of aqueous LacLL-NP1 nanoparticle solution (0.609 µmol nanoparticle) (low concentration of targeting ligand) was concentrated by centrifuge filtration (AMICON, 4 mL, 10 kDa) and washed once with $Na_2CO_3/NaHCO_3$ buffer (0.1 M, pH 9.3). The residual solution was solved in 1.5 mL of the buffer. To the NP solution a sulfo-rhodamine B acid chloride solution in DMF (133 µL, 9.14 µmol, 5.27 mg) was added and mixture was shaken on an orbital shaker at room temperature overnight shielded from daylight. The reaction mixture was transferred to a previously washed AMICON filter (4 mL, 10 kDa). Nanoparticle solution was centrifuged and repeatedly washed three times with $Na_2CO_3/NaHCO_3$ buffer (0.1 M, pH 9.3) and repeatedly with Milli-Q water until the filtrate appears colorless. Finally, the nanoparticles were collected in 3 mL Milli-Q water. The nanoparticles were characterized by $^1$H NMR after KCN/KOH etching, DLS, TEM and zeta potential. The gold concentration of the nanoparticle solution was determined by ICP-MS.

Example 3—Liver Targeting of Nanoparticles Demonstrated In Vivo

The liver targeting properties of lactose long linker gold nanoparticles could be shown by comparison of different nanoparticle constructs in an in vivo biodistribution study. Two lactose long linker nanoparticles with a high and a low content of the liver targeting molecule (LacLL-NP1 (low)+ LAcLL-NP2 (high)), two similar lactose short linker nanoparticles (LacSL-NP1 (low)+LacSL-NP2 (high)) (the lactose is linked to a C2 linker), and non-targeting nanoparticle (Glc-NP), respectively, were intravenously injected to mice.

Figure 6:
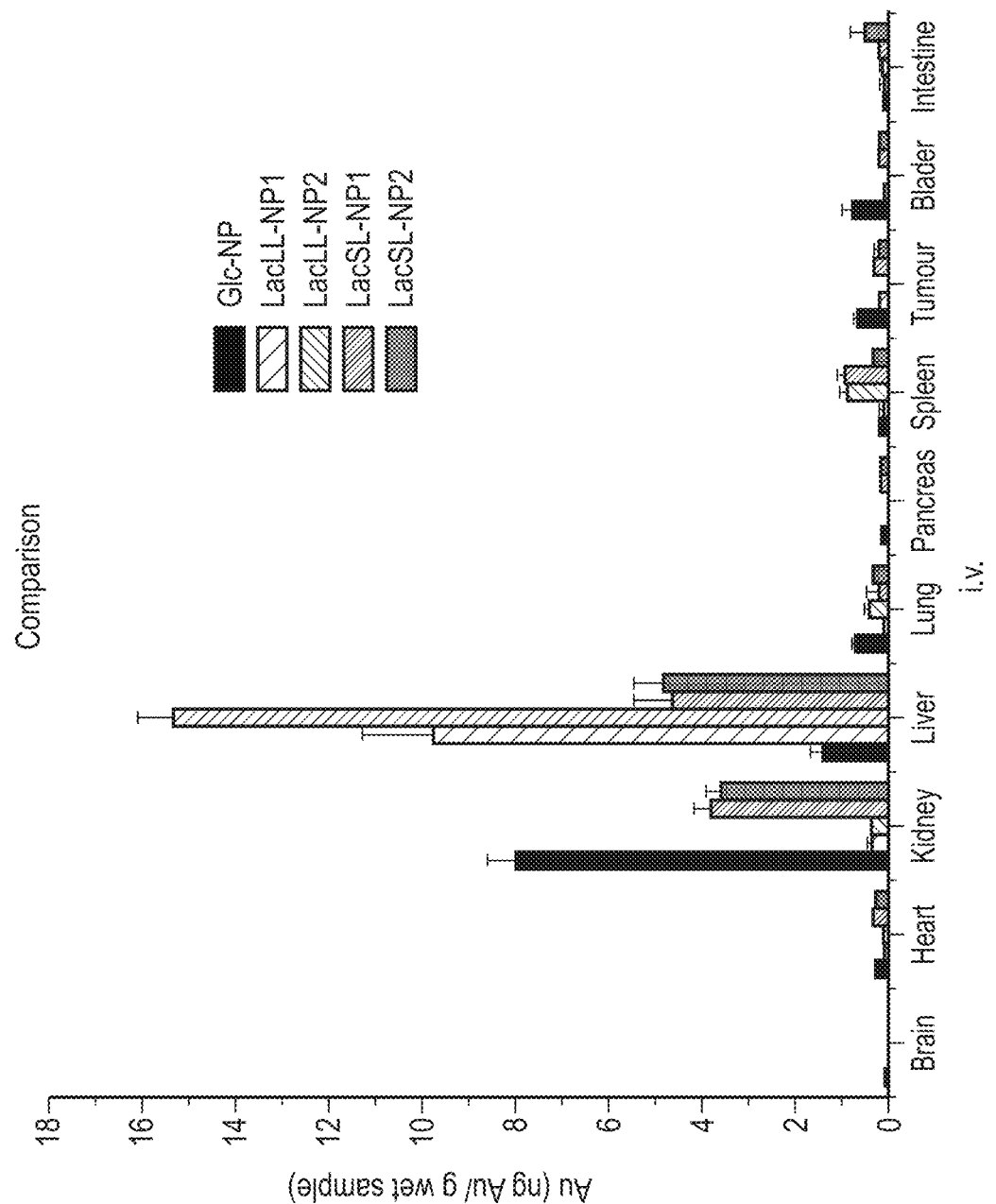
FIG. 6 shows ICP-MS results for accumulation of rhodamine-conjugated GNPs in various organs in the body. From left to right, the x axis reads: brain, heart, kidney, liver, lung, pancreas, spleen, tumour, bladder, and intestines. MBLB-0126-012 is the control, MBLB-126-078 is LacLL-NP2, MBLB-135-042 is LacLL-NP1, MBLB-126-082 is LacSL-NP1, and MBLB-126-084 is LacSL-NP2.

After 90 minutes circulation time the animals were sacrificed, the main organs were harvested and analysed by ICP-MS to determine the gold concentration in the organs. The plotting of these data provided a biodistribution map for the different constructs (FIG. 6). As expected, the liver targeting constructs were mainly found in the liver, whereas the non-targeting nanoparticle was accumulated in the kidneys. It was observed that the linker length of the liver targeting molecule influences the liver uptake of the gold nanoparticle. For the short linker version 42-46% of the total found gold amount was present in the liver. By contrast, for the long linker constructs almost all gold was detected in the liver (up to 91%).

This experiment demonstrates that suitable payloads can highly efficient directed to the liver using liver targeting lactose long linker gold nanoparticles.

Experimental Section

Cell Lines and Transfection

Hepatocarcinoma cell line, HepG2, cells were grown in DMEM (Sigma Aldrich) supplemented with 10% FCS (Gibco) at 37° C., 95% air and 5% $CO_2$, in 10-cm petri dishes (BD), washed with PBS 1× (Sigma Aldrich) and passaged upon treatment with Trypsin-EDTA 0.05% (Gibco). Viable cells were counted in a hemocytometer in a trypan blue exclusion assay. HepG2 cells were regularly tested for mycoplasma using a set of primers common to all members of genus *Mycoplasma* (Choppa et al, 1998). Cells were seeded at a density of 2-3 $10^4$ cells/cm$^2$ in a 6-well plate and subsequently transfected with 1:3 and 1:5 molar ratios of pEGFP-Luc vector (Clontech) and PEI25 (Sigma-Aldrich). Upon transfection, cells were selected by adding 800 µg/µL G418 to the culture medium for forty-eight hours. Subsequently, cells were maintained in fresh medium and grown until confluence. In order to assess the in vitro bioluminescence signal a simple luciferase assay with the aid of a Mithras multimode plate reader by adding D-Luciferase to cell lysates in CCLR buffer was performed (25 mM Tris-HCl pH 7.8, 2 mM DTT, 2 mM EGTA, 10% glycerol, 1% Triton X-100).

Animal Housing

Seventy female BALB/c nude mice (6 weeks old) were purchased from an authorized provider (Janvier Labs). All mice were housed in laminar-flow cabinets under specific pathogen-free conditions at room temperature with a 12-hour light/dark cycle and fed with pellets and water ad libitum. The Experimental Animal Committee of USC approved the animal study; consequently, all animal experiments meet the Animal Welfare guidelines.

Xenografts & In Vivo Near-Infrared Fluorescence Imaging

Log growth-phase of HepG2 cells ($10^5$ cells in 0.1 ml PBS) were injected to subcutaneously into the left flank of athymic nude mice (n=6 each experimental group) to establish the model of tumor-bearing mice. Tumour implantation was regularly checked by visual inspection and finally confirmed by registration of bioluminescent signal in an IVIS Spectrum (Caliper LifeSciences). D-Luciferin was administered (150 mg/kg) in order to co-localize the bioluminescence in tumour cells with the fluorescent NPs. Mice bearing tumours were be split into 5 groups (control group included), six mice each. Tumour volume were calculated by the formula: [(length$^2$×width)/2](Soengas et al., 1999). Once the tumours reached a volume of 400 mm$^3$ nanoparticles were administered i.v.

In vivo fluorescence imaging was acquired using an IVIS Spectrum (Caliper LifeSciences) for detection of the rhodamine-conjugated GNPs at 0 min, 45 min, and 90 min after injection. Mice were anesthetized using isoflurane during image acquisition, and upon the acquisition of fluorescence/bioluminescence images were euthanized (at 90 min after injection) and their organs (brain, lungs, heart, liver, spleen, pancreas, gut, bladder and kidneys) and the tumor harvested for subsequent ICP-MS analysis.

ICP-MS results

| | Brain | Heart | Kidney | Liver | Lung | Pancreas | Spleen | Tumour | Bladder | Intestine |
|---|---|---|---|---|---|---|---|---|---|---|
| | | | | μg Au/g wet sample | | | | | | |
| Glc-NP | 0.020 | 0.236 | 7.988 | 1.419 | 0.710 | 0.138 | 0.188 | 0.691 | 0.800 | 0.112 |
| LacLL-NP1 | 0.006 | 0.066 | 0.286 | 15.322 | 0.451 | 0.030 | 0.909 | 0.039 | 0.019 | 0.135 |
| LacLL-NP2 | 0.002 | 0.064 | 0.360 | 9.749 | 0.072 | 0.023 | 0.092 | 0.188 | 0.085 | 0.114 |
| LacSL-NP1 | 0.015 | 0.292 | 3.807 | 4.622 | 0.213 | 0.172 | 0.938 | 0.303 | 0.218 | 0.208 |
| LacSL-NP2 | 0.013 | 0.277 | 3.571 | 4.826 | 0.329 | 0.167 | 0.326 | 0.230 | 0.205 | 0.537 |

Figure 7:
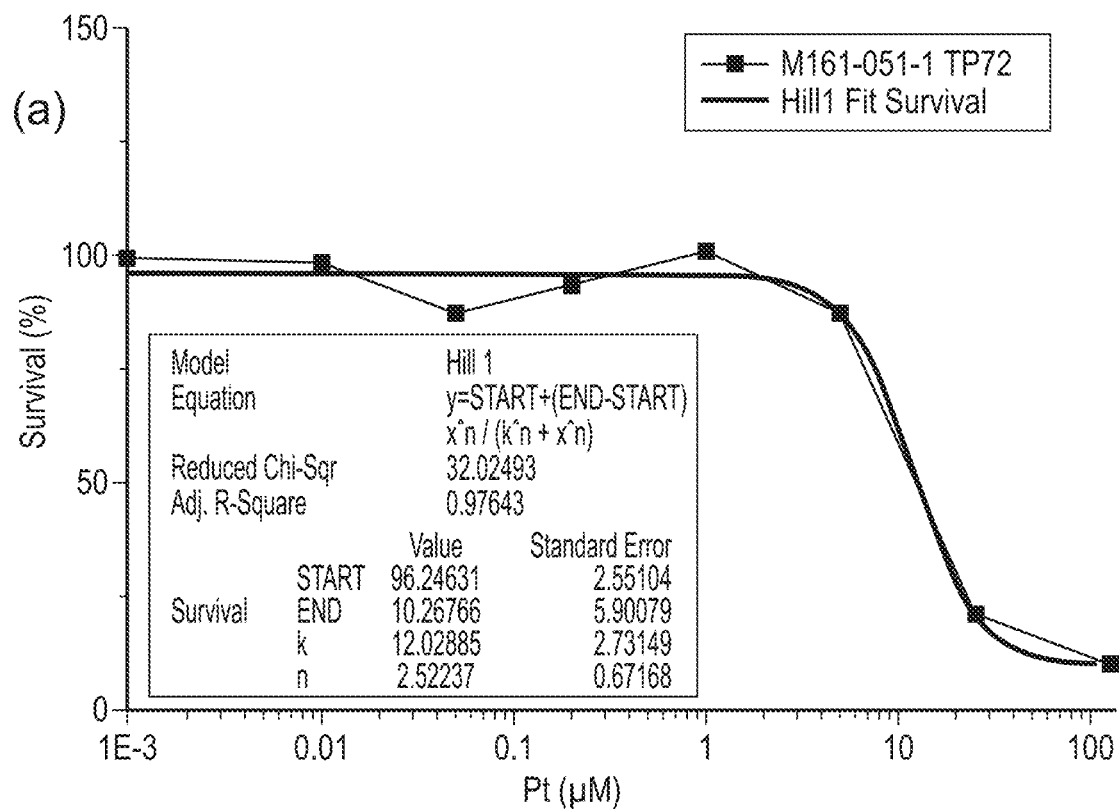
FIG. 7 shows MTT cell viability assay results 72 h after treatment with (a) Pt-LacLL-NP, (b) free Pt, (c) Doxo-LacLL-NP and (d) free doxorubicin.
Figure 7:
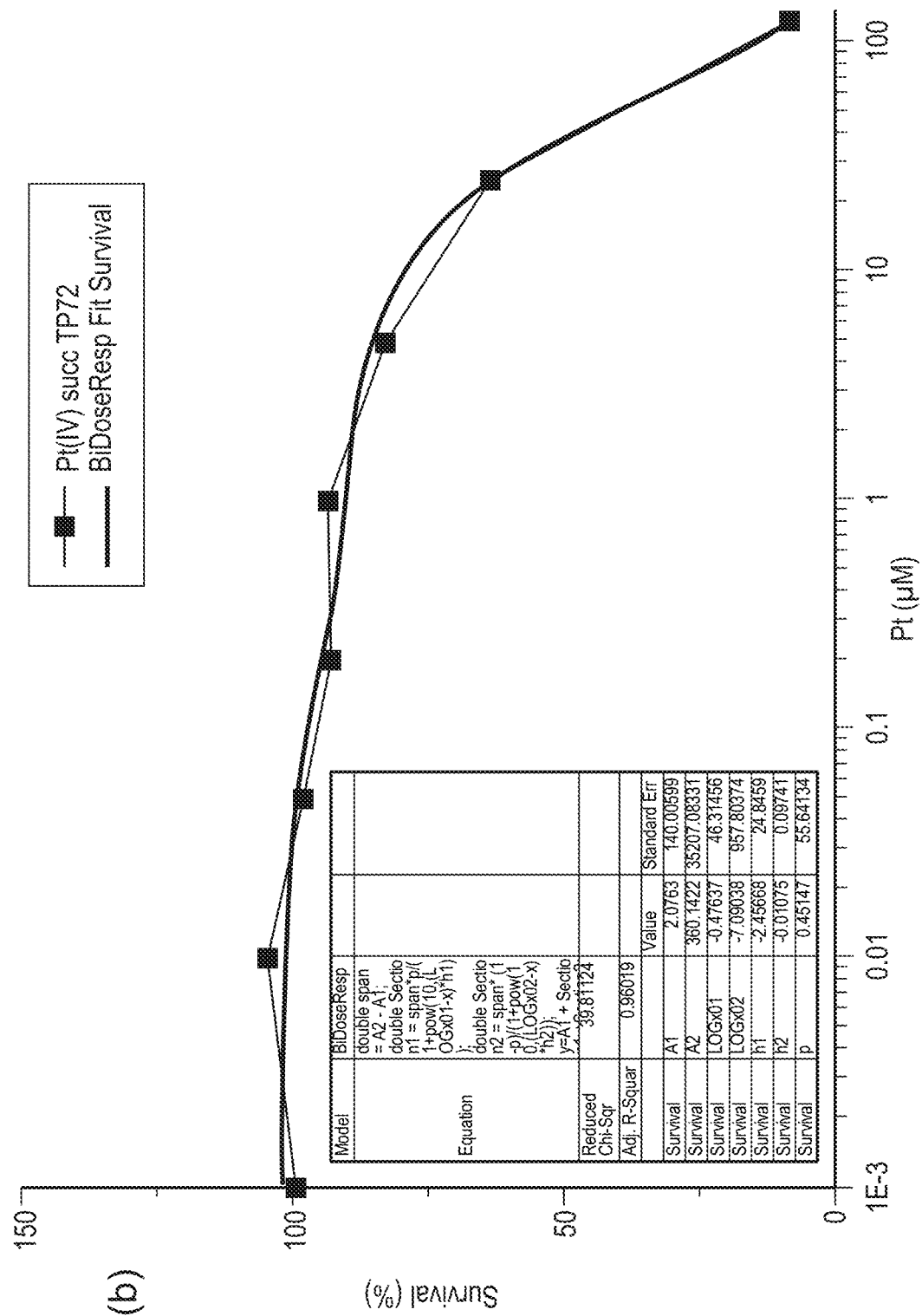
Figure 7:
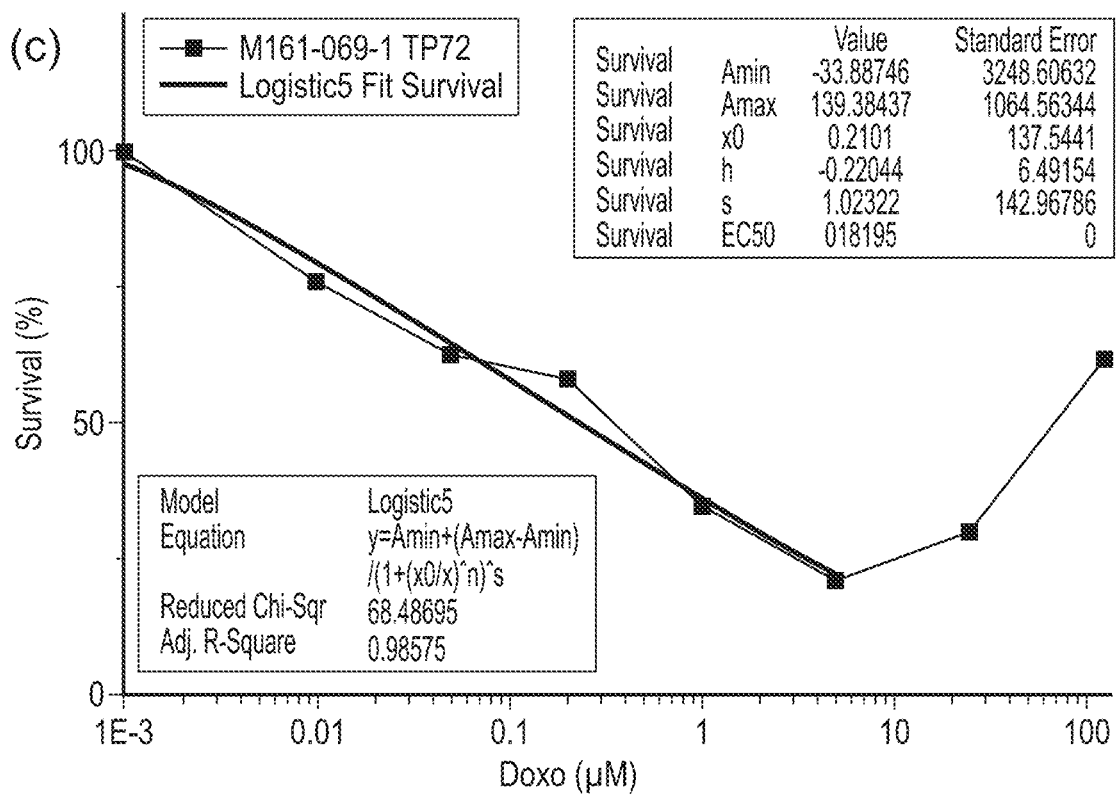
Figure 7:
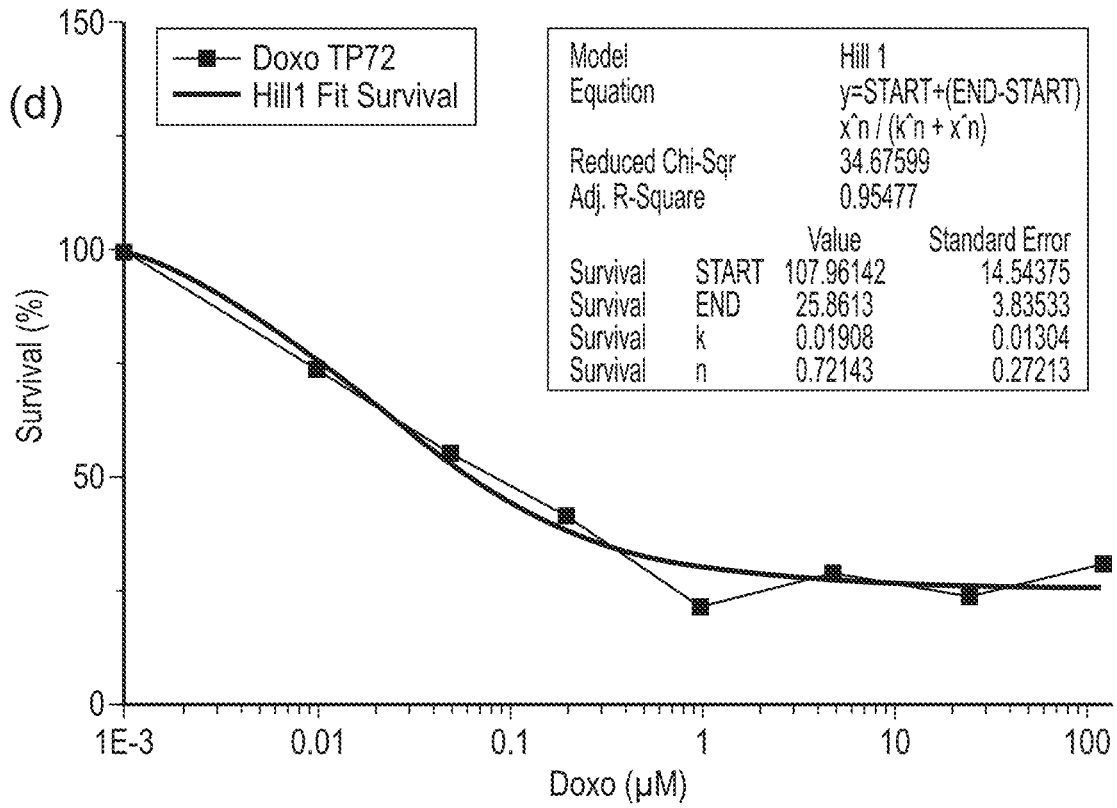

Example 4—In Vitro Cytotoxicity with Liver Targeting Lactose Long Linker Gold Nanoparticles Carrying a Chemotherapeutic Pay Load The cytotoxicity of liver targeting lactose long linker gold nanoparticles pay-loaded with the chemotherapeutics Pt(IV)-succinate (Pt-LacLL-NP+platinum) and doxorubicin (Doxo-LacLL-NP+doxorubicin) was tested in comparison with the free drug in a MTT (3-(4,5-dimethylthiazol-2-yl)-2,5-diphenyltetrazolium bromide) cell viability assay (FIG. 7). The human hepatocellular carcinoma cell line HepG2 was used in the assay.

In the case of the platinum based antineoplastic agent Pt(IV)-succinate, it was demonstrated that the Pt-LacLL-NP is more potent than the free drug. For the nanoparticle, an IC50 value of 12.8 μM was observed, whereas for the free drug a value of 38.6 μM could be found. For doxorucibin, the free compound showed a slightly higher cytotoxicity in comparison to the pay-loaded nanoparticle. The attachment of the drug to the nanoparticle maintained the chemotherapeutic activity and allows the use of liver targeting lactose long linker gold nanoparticles as a drug delivery system.

MTT assay results

| Compound | IC$_{50}$ (μM) |
|---|---|
| Pt-LacLL-NP | 12.78 |
| Platinum | 38.61 |
| Doxo-LacLL-NP | 0.24 |
| Doxorubicin | 0.06 |

EXPERIMENTAL SECTION

Cell Seeding in 96-Well Microtiter Plates

HepG2 cells were grown in a T-75 flask. For the transfer of the cell the medium was removed from the flask and the cells were trypsinated for 5 minutes. The cells were collected in a Falcon tube and diluted with complete cell medium. The cell counting was conducted in a Neubauer chamber. A cell solution was prepared to seed 4000 cells per well (200 μL per well). The microtiter plate was incubated for 24 h at 37° C.

Treatment of Seeded HepG2 Cell

For each NP and drug, formulations in cell medium were prepared. The compounds were tested in different concentrations (0.01, 0.05, 0.2, 1, 5, 25 and 125 μM based on drug amount). For the treatment, the cell medium was removed from all wells and exchanged for drug formulations. 200 μl of treatments per triplicate was added to each well. The microtiter plates were incubated for 24 h, 48 h and 72 h at 37° C.

MTT Measurement 24 h, 48 h and 72 h after Treatment 1.5 mL MTT solution (8.0 mg in 1.6 mL DMSO) was diluted with complete cell medium (phenol-red free). The treatment cell medium was removed from the microtiter plate, the wells were washed with 100 μL PBS and 100 μL of the MTT reactive solution was added to each well. After one hour incubation at 37° C. the MTT solution was removed and 100 μL DMSO was added to dissolve the formazan dye. Absorbance was measured at 570 nm.

Statistical Analysis and IC50 Calculation

Data were analysed using OriginPro8. The normalized data were plotted and the curve was fitted using a non-linear regression curve fit (sigmoidal dose-response curve with variable slope). The Absolute IC50 values were obtained by interpolation.

Example 5—Selection of Targeted GNPs and HCC Targeting In Vitro

Several base/peptide targeted GNPs were screened in vitro. GNPs having a mixed corona comprising galactose-C2-SH (Gal-C2) ligands and HSPEG8COOH were synthesised according to methodology analogous to that described above in Examples 1 and 2, with however galactose-C2-SH replacing glucose-C2-SH and HSPEG8COOH (also abbreviated SH-EG$_6$-COOH or SH—(OCH$_2$CH$_2$)$_6$-COOH) replacing the amino linker NH$_2$-EG$_6$-SH.

The Au@Gal-C2:HSPEG8COOH GNPs were found to exhibit lower non-specific binding (normal:tumour cells) and good plasma circulation in vivo. The corona of Gal-C2 and HSPEG8COOH was therefore selected for HCC targeting studies using glypican-3 binging peptides.

Figure 8:
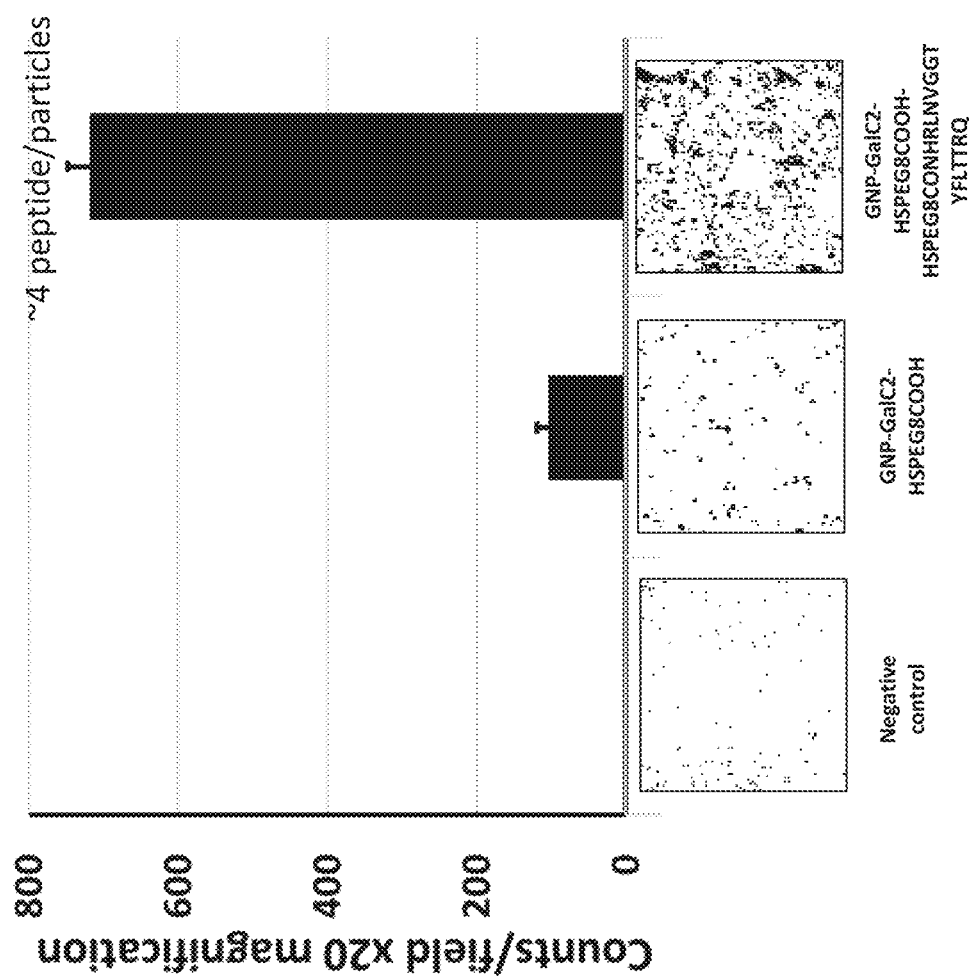
FIG. 8 shows in vitro targeting of GNPs to HCC cells measured as counts per field at 20× magnification. The left-hand panel shows a lack of counts exhibited by the negative control. The middle panel and bar shows counts for GNPs having a corona of galactose-C2 ligands and HSPEG8COOH ligands. The right-hand panel and bar shows counts for GNPs with a corona of galactose-C2 ligands and HSPEG8COOH ligands, in which a proportion of the HSPEG8COOH ligands have conjugated thereto the glypican-3-binding peptide, RLNVGGTYFLTTRQ (SEQ ID NO: 1), via its N-terminus (approx. 4 peptide molecules per nanoparticle). It is immediately evident that the GNPs having the glypican-3-binding peptide exhibit significantly increased targeting to HCC cells compared with GNPs lacking the glypican-3-binding peptide (approx. 7-fold increased targeting).

The glypican-3 peptide described in U.S. Pat. No. 8,388,937B2 (the contents of which are expressly incorporated herein by reference)—see SEQ ID NO: 1 thereof, which has the amino acid sequence: RLNVGGTYFLTTRQ (SEQ ID NO: 1) was linked to the terminal COOH group of a proportion of the HSPEG8COOH ligands via the N-terminus of said peptide. In a "high loading" GNP construct (see row 1 in the table below), approximately 4 peptides were linked per nanoparticle core. The "high loading" Au@Gal-C2:HSPEG8COOH:HSPEG8CONHRLNVGGTYFLTTRQ GNPs were found to exhibit approximately 7-fold targeting relative to the base GNP lacking the RLNVGGTYFLTTRQ peptide (see FIG. 8 and the first row of the following table). The "low loading" Au@Gal-C2:HSPEG8COOH:HSPEG8CONHRLNVGGTYFLTTRQ GNPs (see row 3 of the following table) exhibited approximately 4.6-fold targeting relative to the base GNP lacking the RLNVGGTYFLTTRQ peptide.

| GNP-Construct | Fold-targeting (over base particle) |
|---|---|
| GNP-GalC2-HSPEG8COOH-HSPEG8CONHRLNVGGTYFLTTRQ "high loading" | 7.1 |
| GNP-GalC2(50)-AL(50)-(Ac)YFLTTRQ | 5.0 |
| GNP-GalC2-HSPEG8COOH-HSPEG8CONHRLNVGGTYFLTTRQ "low loading" | 4.6 |

Further investigation has been carried out in which the orientation and/or terminal capping of the linked RLNVGGTYFLTTRQ peptide was evaluated. In particular, RLNVGGTYFLTTRQ (attached to PEG8COOH via the N-terminus, free COOH terminus—described above) and RLNVGGTYFLTTRQ-NH2 (attached to PEG8COOH via the N-terminus, primary amide terminus replacing the standard C-terminus).

A further construct that has been investigated comprises a mixed corona of galactose-C2-SH and amino linker (also known as "AL" or $NH_2$-$EG_6$-SH) in approximately 50:50 ratio. The RLNVGGTYFLTTRQ peptide was attached to the amino linker via the C-terminus of the peptide or by using an acyl-N-terminal version of the peptide and attaching the acyl-N-terminus of the peptide to the amino linker. Two methods were employed: (1) the peptide was attached to GNP-AL via the C-terminus (giving a positive particle); or (2) the peptide was attached to AL-SH in a first step and the SH-$EG_6$-NHCO-RLNVGGTYFLTTRQ used as a ligand in the nanoparticle synthesis giving a negative particle. The resulting particle may be represented as: Au@GalC2:AL:AL-(Ac)-RLNVGGTYFLTTRQ.

A Further glypican-3-binding peptide described in U.S. Pat. No. 8,388,937B2 (the contents of which are expressly incorporated herein by reference)—see SEQ ID NO: 10 thereof, which has the amino acid sequence: YFLTTRQ (SEQ ID NO: 2) was linked to GNP ligands as follows. A GNP having a mixed corona of galactose-C2-SH and amino linker ($NH_2$-$EG_6$-SH) in approximately 50:50 ratio had the YFLTTRQ peptide linked to the amino linker via an acyl N-terminus of the YFLTTRQ peptide to yield a GNP which may be represented by the following formula: Au@GalC2:AL:AL-(Ac)-YFLTTRQ. Further GNPs produced or contemplated herein include: Au@GalC2:HSPEG8CONH-YFLTTRQ (attached to PEG8COOH via the N-terminus, free COOH terminus) and Au@GalC2:HSPEG8CONH-YFLTTRQ-NH2 (attached to PEG8COOH via the N-terminus, primary amide terminus). As can be seen from row 2 of the above table, the GNP Au@GalC2:AL:AL-(Ac)-YFLTTRQ exhibited approximately 5-fold targeting to HCC cells compared with the base nanoparticle, lacking the YFLTTRQ peptide. These results therefore show that glypican-3-binding peptides contribute to HCC targeting and that higher peptide loading (i.e. more glypican-3 binding peptides per nanoparticle) increases HCC targeting further.

Example 6—GLY-3 Targeted GalC2 GNP Shows HEPG2 Cell Toxicity with a DM4 Payload

The following GNP constructs were synthesised in order to assess their tumour cell killing capability against HepG2 (liver hepatocellular carcinoma) cells:

GNPs with a corona of galactose-C2 and HSPEG8COOH ligands (40:60 ratio), which may be represented by Au@GalC2:HSPEG8COOH.

GNPs with a corona of galactose-C2, HSPEG8COOH and maytansinoid DM4 ligands, which may be represented by Au@GalC2:HSPEG8COOH:DM4.

GNPs with a corona of galactose-C2, HSPEG8COOH and maytansinoid DM4 ligands, wherein a proportion of the HSPEG8COOH ligands are conjugated to the N-terminus of the glypican-3-binding peptide RLNVGGTYFLTTRQ (SEQ ID NO: 1)<1 peptide per nanoparticle. The GNPs may be represented by: Au@GalC2:DM4:HSPEG8COOH:HSPEG8CONHRLNVGGTYFLTTRQ.

Free maytansinoid DM4 was also used as a positive control in the HepG2 cell toxicity experiments.

Figure 9:
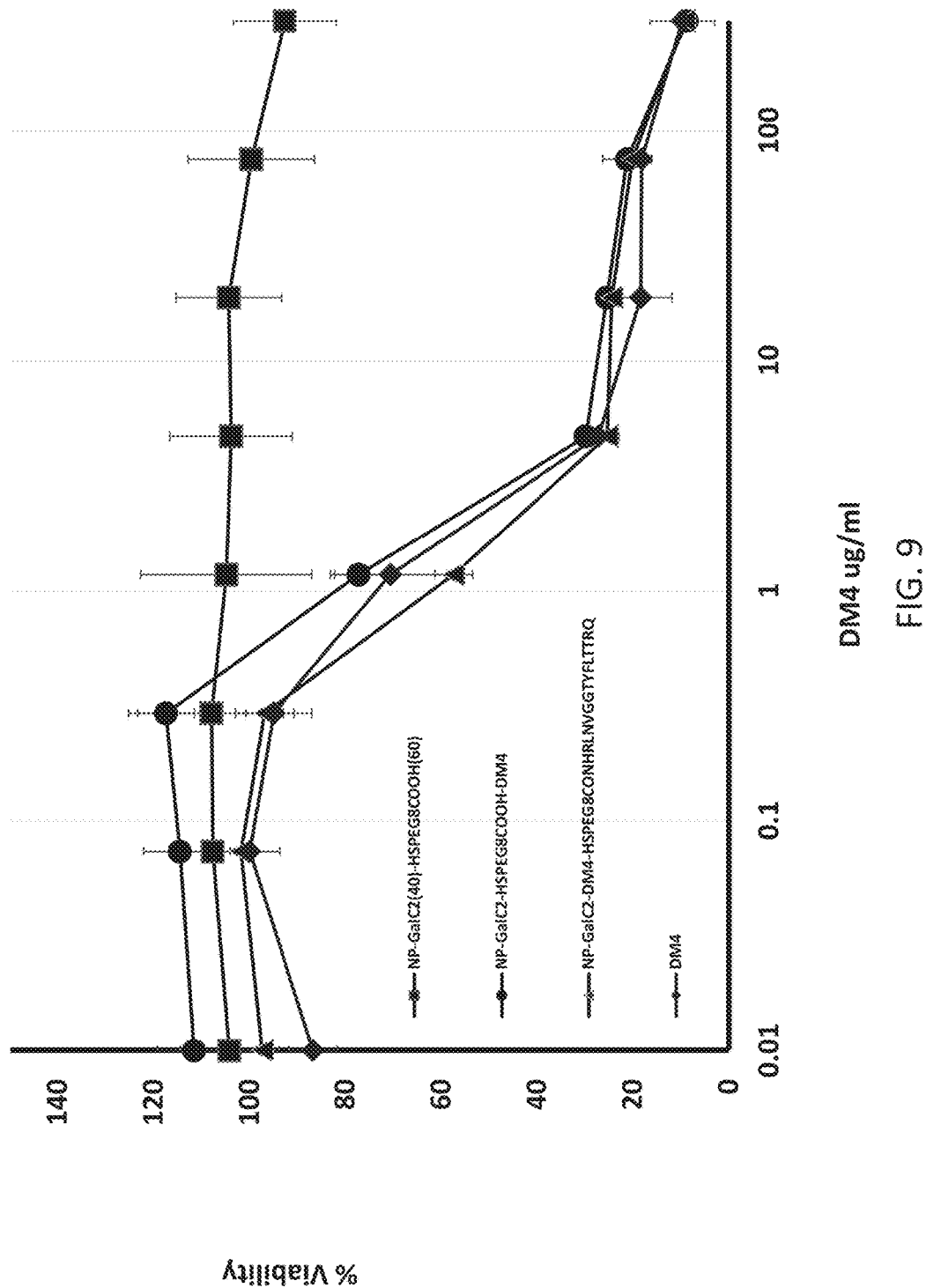
FIG. 9 shows the effect of various GNP constructs, and of free maytansinoid DM4, on cell viability on HEPG2 cells following 72 hours treatment at the indicated concentrations. Cell viability measured as percentage control in an MTT assay is plotted against concentration (of DM4 where present) in μg/ml (note the log scale of the x-axis). GNPs with a corona of galactose-C2 and HSPEG8COOH ligands (40:60 ratio) are shown with squares. This GNP, lacking DM4, exhibits essentially no toxicity under the conditions tested. GNPs with a corona of galactose-C2, HSPEG8COOH and DM4 ligands are shown with circles. The dose-toxicity curve closely resembles that of free DM4 shown with diamonds. GNPs with a corona of galactose-C2, HSPEG8COOH and DM4 ligands, wherein a proportion of the HSPEG8COOH ligands are conjugated to the N-terminus of the glypican-3-binding peptide RLNVGGTYFLTTRQ (SEQ ID NO: 1)—approx. <1 peptide per nanoparticle—are shown with triangles. The dose-toxicity curve for these DM4 and glypican-3-binding peptide-loaded GNPs closely resembles that of free DM4 shown with diamonds.

The effect of the various GNP constructs, and of free maytansinoid DM4, on cell viability on HEPG2 cells following 72 hours treatment is shown in FIG. 9. Cell viability measured as percentage control in an MTT assay is plotted against concentration. The GNP lacking DM4 exhibited essentially no toxicity under the conditions tested. Both the GNPs with DM4 exhibited dose-toxicity curves that closely resembled that of free DM4. Taken together with the HCC targeting demonstrated by the GNPs having glypican-3-binding peptide as liver targeting agents (see Example 5), these results indicate that GNPs having a mixed corona of a dilution ligand, a glypican-3-binding peptide, and a chemotherapeutic such as maytansinoid DM4 is expected to demonstrate selected liver cancer cell killing while minimising off-target effects (i.e. minimising toxicity against healthy cells).

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A nanoparticle comprising:
a core comprising a metal, wherein the diameter of the core is in the range 1 nm to 5 nm, as determined by transmission electron microscopy (TEM); and
a plurality of ligands covalently linked to the core, wherein said ligands comprise:
(i) at least one liver-targeting ligand which is an asialoglycoprotein receptor (ASGPR) binding agent comprising a carbohydrate, wherein the liver-targeting ligand is covalently linked to the core via a liver-targeting ligand linker that comprises:
—(CH$_2$)$_n$—, wherein n is at least 5; and/or
—(OCH$_2$CH$_2$)$_m$—, wherein m is at least 3;
(ii) at least one payload ligand comprising a bioactive agent which is a small molecule organic compound that is cytotoxic; and
(iii) a plurality of dilution ligands each comprising a carbohydrate which is a monosaccharide, wherein said dilution ligands are each covalently bound to the core via a dilution ligand linker having a chain length of 2 to 4 atoms, and
wherein the total number of said plurality of ligands covalently linked to the core is at least 20, and wherein the diameter of the nanoparticle including its ligands is not more than 50 nm, and wherein said dilution ligands make up between 10% and 70% of the total number of ligands of the nanoparticle.

2. The nanoparticle according to claim 1, wherein said liver-targeting ligand linker is bound to the core via a terminal sulphur atom.

3. The nanoparticle according to claim 1, wherein the payload ligand comprises a compound selected from the group consisting of: maytansinoid DM4, doxorubicin, irinotecan, Platinum (II), Platinum (IV), temozolomide, carmustine, camptothecin, docetaxel, sorafenib, maytansine, maytansinoid DM1, monomethyl auristatin E (MMAE) and panobinostat.

4. The nanoparticle according to claim 1 wherein the nanoparticle further comprises at least one further payload ligand comprising a detectable label.

5. The nanoparticle according to claim 1, wherein the at least one dilution ligand comprises glucose or galactose.

6. The nanoparticle according to claim 1, wherein said dilution ligand linker comprises —(CH$_2$)$_n$—, wherein n=2 to 3.

7. The nanoparticle according to claim 6, wherein said dilution ligand linker is bound to the core via a terminal sulphur atom.

8. The nanoparticle according to claim 1, wherein the core comprises at metal selected from the group consisting of: Au, Ag, Cu, Pt, Pd, Fe, Co, Gd, Zn or any combination thereof.

9. The nanoparticle according to claim 8, wherein the core comprises gold.

10. A pharmaceutical composition comprising a plurality of nanoparticles of claim 1 and at least one pharmaceutically acceptable carrier or diluent.

11. The pharmaceutical composition according to claim 10, wherein the composition is in injectable form.

12. A method of treating a liver disorder in a mammalian subject, comprising administering a nanoparticle according to claim 1 to a mammalian subject in need of therapy.

13. The method according to claim 12, wherein said liver disorder comprises a primary or secondary cancer of the liver.

14. The method according to claim 13, wherein said cancer is hepatocellular carcinoma (HCC).

15. The method according to claim 13, wherein said cancer is selected from: heptoblastoma, cholangiocarcinoma, cholangiocellular cystadenocarcinoma, angiosarcoma, hemangioendothelioma, embryonal sarcoma, fibrosarcoma, leiomyosarcoma and rhabdomyosarcoma.

16. The nanoparticle according to claim 1, wherein said ASGPR binding agent comprises galactose.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: glypican-3 binding peptide

<400> SEQUENCE: 1

Arg Leu Asn Val Gly Gly Thr Tyr Phe Leu Thr Thr Arg Gln
1               5                   10
```

```
<210> SEQ ID NO 2
<211> LENGTH: 7
<212> TYPE: PRT
<213> ORGANISM: Artificial Sequence
<220> FEATURE:
<223> OTHER INFORMATION: glypican-3 binding peptide

<400> SEQUENCE: 2

Tyr Phe Leu Thr Thr Arg Gln
1               5
```